US009981895B1

(12) United States Patent
Clayton et al.

(10) Patent No.: US 9,981,895 B1
(45) Date of Patent: May 29, 2018

(54) COMPOSITIONS AND METHODS OF SYNTHESIZING ARACHIDIN-3 FROM RESVERATROL

(71) Applicant: Parnative, Inc., Jonesboro, AR (US)

(72) Inventors: Benjamin Clayton, Pikeville, KY (US); Jeremy Bandy, Bedfor, VA (US)

(73) Assignee: Parnative Inc., Jonesboro, AR (US)

( * ) Notice: Subject to any disclaimer, the term of this patent is extended or adjusted under 35 U.S.C. 154(b) by 18 days.

(21) Appl. No.: 15/083,707

(22) Filed: Mar. 29, 2016

Related U.S. Application Data

(60) Provisional application No. 62/140,450, filed on Mar. 30, 2015.

(51) Int. Cl.

| C07C 39/23 | (2006.01) |
|---|---|
| C07C 37/68 | (2006.01) |
| C07C 37/20 | (2006.01) |
| A61K 31/05 | (2006.01) |
| A61K 9/00 | (2006.01) |
| A23L 1/30 | (2006.01) |

(52) U.S. Cl.
CPC ............ *C07C 39/23* (2013.01); *A23L 1/3002* (2013.01); *A61K 9/0053* (2013.01); *A61K 31/05* (2013.01); *C07C 37/20* (2013.01); *C07C 37/68* (2013.01); *A23V 2002/00* (2013.01)

(58) Field of Classification Search
CPC ................................................. C07C 37/20
See application file for complete search history.

(56) References Cited

U.S. PATENT DOCUMENTS

| 7,666,677 B2 | 2/2010 | Medina-Bolivar et al. |
| 2008/0032372 A1 | 2/2008 | Medina-Bolivar et al. |

(Continued)

FOREIGN PATENT DOCUMENTS

KR 20120056586 6/2012

OTHER PUBLICATIONS

KR20120056586, pp. 1-9; English translation (Year: 2012).*

(Continued)

*Primary Examiner* — Medhanit W Bahta
(74) *Attorney, Agent, or Firm* — Carrie Stroup

(57) ABSTRACT

Composition, methods of synthesizing trans-arachidin-3; and, methods of use as a dietary supplement, food additive, pharmaceutical, nutraceutical, cosmeceutical, and antioxidant. The methods of production entail organic syntheses using primary alkylamines or primary hydroxyalkyl amines, or carboxy amines (amino acids) with natural carboxylic acids (acetic acid) as catalysts to react isovaleraldehye with trans-resveratrol. The synthesis is carried out in organic solvent, which is composed of an azeotropic mixture comprising toluene with pyridine, n-butanol, n-propanol, 2-propanol, 2-methyl-1-propanol, or other alcohols that form an azeotrope with toluene. The final product is purified and analyzed for the amount of trans-arachidin-3, such as via HPLC, IR, column chromatography, and high-performance counter-current chromatography. All solvent and catalysts used in the reaction are approved by the FDA as either food additives, secondary direct food additives, and/or indirect food additives, and thus this synthetic trans-arachidin-3 may be used in the food and cosmetic industry.

9 Claims, 30 Drawing Sheets

Scheme 1

Scheme 2

Scheme 3

(56) References Cited

U.S. PATENT DOCUMENTS

2010/0130623 A1    5/2010  Medina-Bolivar et al.
2012/0165281 A1*   6/2012  Radominska-
                            Pandya .............. A61K 31/7034
                                                          514/35

OTHER PUBLICATIONS

Abott, J. A. et al. "Purification of Resveratrol, Arachidin-1, and Arachidin-3 from Hairy Root Cultures of Peanut (*Arachis hypogaea*) and Determination of Their Antioxidant Activity and Cytotoxicity" Biotechnol. Prog., 2010, vol. 26, No. 5 (Year: 2010).*
Park, B.H., et. al. "Total Synthesis of Chiricanine A, Arahypin-1, trans-Arachidin-2, trans-Arachidin-3, and Arahypin-5 from Peanut Seeds," Journal of Natural Products, 2011, 74:644-649.

* cited by examiner

COMPOSITIONS AND METHODS OF SYNTHESIZING ARACHIDIN-3 FROM RESVERATROL

This application claims priority to the following U.S. Provisional Patent Application No. 62/140,450, entitled "Compositions and Methods of Synthesizing Arachidin-3 from Resveratrol", by Clayton et al, filed Mar. 30, 2015.

FIELD OF THE DISCLOSURE

The present disclosure generally relates to methods of chemically synthesizing a non-toxic trans-arachidin-3, and methods of use of the synthesized arachidin-3 in compositions for treating humans.

BACKGROUND OF THE DISCLOSURE

The role of micronutrients in the diet has become well established. Commercial processes often deplete foods of essential micronutrients and/or people often lack the will to maintain a balanced diet, which leads society to being at a greater risk for debilitating diseases such as cancer, cardiovascular, and/or neurodegenerative diseases. Several cancers have been shown to be in large part preventable through changes in lifestyle, which includes a well-balanced diet.

Thus, there is a need to put back into foods and beverages the beneficial, bioactive components that are being lost in the American diet. Low cost production of nutraceuticals will enhance the ability to fortify foods and beverages with chemo-preventive and/or neuro-, cardio-protective agents, such as trans-arachidin-3 (FIG. 1B).

Arachidin-3 is a natural derivative of the well-established nutraceuticals/phytonutrient known as resveratrol (FIG. 1A, trans-resveratrol; and, FIG. 1C, cis-resveratrol), which is a key bioactive component in red wines. It is also a naturally occurring medicinal compound found in various plants such as the peanut plant, but only in low abundance. Arachidin-3 has value to humans and animals as a dietary supplement, food additive, pharmaceutical precursor (lead compound), nutraceutical, cosmeceutical, and antioxidant.

The low cost production of nutraceuticals, such as arachidin-3, requires cheap production routes via extraction from common plants and/or synthetic strategies. Extraction and synthetic strategies must satisfy regulations from the Food and Drug Administration (FDA) for use as a dietary supplement and topical compound. This limits which reagents and solvents can be used to produce the nutraceuticals because many reagents in common use in organic chemical synthesis, such as many organometallic reagents, could be toxic, and thus they must b e eliminated from downstream foods or supplements. Therefore, the development of cheap, facile synthetic strategies using non-toxic reagents can be the most economical and safe route for producing compounds that are not found in high abundance from natural plant sources, such as trans-arachidin-3.

The prior art discloses in KR20120056586A filed Jun. 4, 2012, by Lee et al, and entitled "Synthesis method of compound having a stilbene skeleton", a method of chemically synthesizing trans-arachidin-3 using EDDA as a catalyst and benzene as a solvent, neither of which are FDA approved as food additives and topical contact substances. The reaction also comprises multiple steps that first requires reacting benzaldehyde with benzyl phosphonate in the presence of potassium tert-butoxide in THF to produce an intermediate compound (17) that is subsequently used to produce trans-arachidin-3 (see Scheme 4; Park, B. H., et. al. "Total Synthesis of Chiricanine A, Arahypin-1, trans-Arachidin-2, trans-Arachidin-3, and Arahypin-5 from Peanut Seeds," Journal of Natural Products, 2011, 74:644-649).

Therefore, what is needed within the health industry is an economical and efficient method of chemically synthesizing a non-toxic form of trans-arachidin-3 from naturally occurring resveratrol, or synthetic resveratrol, using only solvents and catalysts that are approved by the Food and Drug Administration, such that the resulting compound is deemed safe for use in mammals (e.g. for human oral consumption and topical applications). It is also advantageous if the method of synthesis is a one-chemical reaction process, and in which all of the synthesis steps can be carried out in the same container, e.g. pot.

SUMMARY OF THE DISCLOSURE

Arachidin-3's IUPAC name is "5-RE)-2-(4-hydroxyphenyl) ethenyl]-2-[(1E)-2-phenylprop-1-en-1-yl]benzene-1,3-diol". The various embodiments of the present disclosure comprise methods of chemically synthesizing non-toxic arachidin-3 from naturally occurring resveratrol, or synthetic resveratrol, as a starting material, and in a one-step chemical reaction.

The various embodiments of the present disclosure further comprise compositions with the synthetically produced arachidin-3, and methods of prevention and treatment of diseases and disorders by administering the compositions to humans and other mammalian animals, such as in a dietary supplement, food additive, pharmaceutical precursor (lead compound), nutraceutical, cosmeceutical, and antioxidant.

In an embodiment, methods of chemically synthesizing a composition or compound comprising arachidin-3 using a single-chemical reaction carried out in the same container (e.g. pot) for at least steps (a)-(d), as disclosed in the various embodiments herein, comprises the following steps. In step (a), adding isovaleraldehyde with synthetic or naturally occurring resveratrol in a solvent comprising an azeotropic mixture with toluene. Step (b): adding a catalyst to the composition produced in step (a). In one or more embodiments, the catalyst is selected from the group consisting of a mixture of a primary alkylamine with a natural carboxylic acid (i.e. acetic acid), a mixture of a primary hydroxyalkyl amine with a natural carboxylic acid (i.e. acetic acid), and a carboxy amine. Step (c): refluxing the composition of step (b). Step (d): purifying out trans-arachidin-3 compound from the composition. Step (e): confirming the synthesis of trans-arachidin-3 by methods well known to the skilled artisan, which comprises by way of non-limiting examples: high purity using column chromatography (neutral); high performance liquid chromatography (HPLC); high performance counter-current chromatography; thin-layer chromatography (TLC; and infrared spectroscopy (IR).

In another embodiment, methods of chemically synthesizing a non-toxic composition or compound comprising arachidin-3 using a single reaction carried out in one pot, as disclosed in the various embodiments herein, comprises the following steps. In step (a): dissolving a reagent of resveratrol into a solvent comprising an azeotropic mixture of toluene. Step (b): adding a reagent isovaleraldehyde. Step (c): adding a catalyst to the composition of step (b). In one or more embodiments, the catalyst is selected from the group consisting of a mixture of a primary alkylamine with a natural carboxylic acid (i.e. acetic acid), a mixture of a primary hydroxyalkyl amine with a natural carboxylic acid (i.e. acetic acid), and a carboxy amine. Step (d): refluxing the composition of step (c). Step (e): purifying out a transarachidin-3 compound from the composition. And wherein steps (a)-(e) were carried out in the same container used for chemical reactions, e.g. the same "pot".

Solvents: The solvent for use in the various embodiments comprise an organic solvent composed of an azeotropic mixture of toluene. The mixture has two roles comprising: dissolving the highly polar resveratrol, and removing water from the reaction, which is a product of this one-reaction conversion. Suitable solvent pairs include, by way of non-limiting examples, azeotropic mixtures of toluene with pyridine, n-butanol, n-propanol, 2-propanol, 2-methyl-1-propanol, or other alcohols that form an azeotrope with toluene.

An advantage of the various embodiments is the use of new catalysts and solvents to carry out the reaction with naturally occurring resveratrol or synthetic resveratrol as a starting material. All solvent and catalysts used in the reaction are approved by the US Food and Drug Administration (FDA) as either food additives, secondary direct food additives, and/or indirect food additives. These approved processing agents include the reagents, solvent, and purifying agents/aids. These FDA approved processing agents or aids are important in order for the synthetic arachidin-3 to be permitted to be sold within products in the food and cosmetic industry.

Another advantage of the various embodiments is the ability to carry out the synthesis in one synthetic step, thus producing a synthetic arachidin-3 efficiently, economically and in high quantity.

The various embodiments of the present disclosure also comprise methods of use. For example, the synthetic compounds disclosed herein may be used: in a method of improving general health by supplementing a user's diet (e.g. as a nutraceutical); and a method of treatment or prevention of a condition, disease or disorder in mammals, e.g. humans, by administering a therapeutic effect amount of a composition comprising synthetic non-toxic arachidin-3, such as trans-arachidin-3. By way of non-limiting examples: the disease or disorder is selected from the group consisting of cancer, coronary heart disease, Alzheimer's, diabetes, hypertension, inflammation and obesity.

For the different methods of use, the composition can be administered via various routes of administration, such as orally, topically, or via injection. Oral administration may further comprise, by way of non-limiting examples: a drinking solution, a pill, a tablet, and a food product. And the composition, no matter its route of administration, may be formulated with other components to produce a "nutraceutical", which is defined herein as a composition (e.g. one comprising synthetic non-toxic arachidin-3, such as trans-arachidin-3) that provides health benefits or possesses medicinal value and that can also have nutritional value. The compositions may further comprise a carrier with solid, semi-solid or liquid diluents, excipients, flavors or encapsulating substances which are suitable for consumption.

The synthetic compounds disclosed herein may also be used as a topical application to treat or prevent a condition or improve the overall health of the user, such as a "cosmeceutical", which is a topically applied cosmetic with medicinal benefits, that is formulated as an ointment, spray, cream, and/or lotion.

BRIEF DESCRIPTION OF THE DRAWINGS

The above and other features, aspects, and advantages of the present disclosure will become better understood with regard to the following description, appended claims, and accompanying drawings where:

DETAILED DESCRIPTION OF EXEMPLARY EMBODIMENTS

Unless otherwise defined, all technical and scientific terms used herein have the same meaning as commonly understood by one of ordinary skill in the art to which this invention belongs. It is also appreciated that certain features of the invention, which are for clarity described in the context of separate embodiments, may also be provided in combination in a single embodiment. Conversely, various features of the invention, which are for brevity described in the context of a single embodiment, may also be provided separately or in any suitable sub-combination. Thus, all combinations of the embodiments are specifically embraced by the present invention and are disclosed herein just as if each and every combination was individually and explicitly disclosed. The term "comprising" as used herein, particularly with regard to a component of a composition or kit or a step of a method, encompasses compositions, kits and methods consisting of or consisting essentially of the component or step.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit, unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

And although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction. And all publications cited herein are incorporated by reference in their entirety.

Figure 1B:
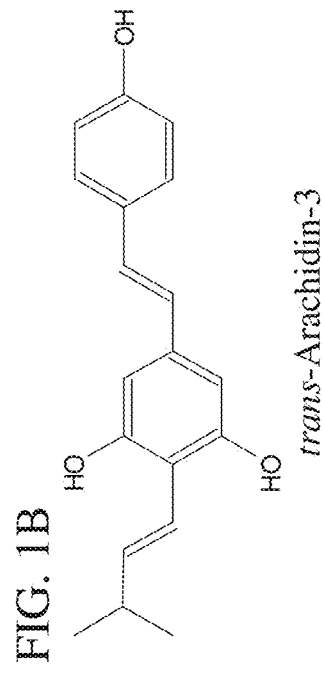
FIG. 1B is a prior art diagram in which the chemical structure of trans-arachidin-3 is shown.
Figure 1A:
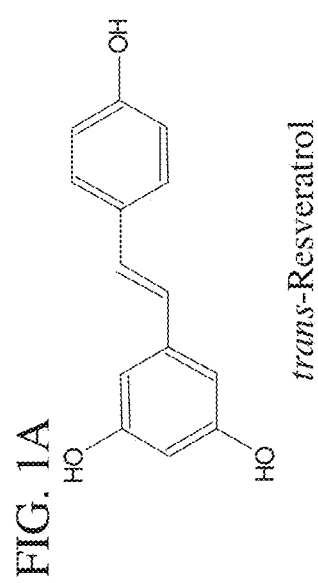
FIG. 1A is prior art diagram in which the chemical structure of trans-resveratrol is shown.
Figure 1C:
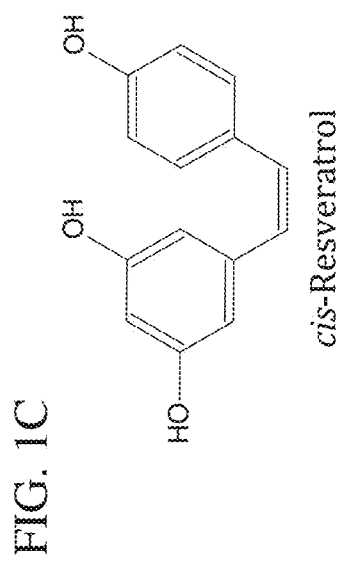
FIG. 1C is a prior art diagram in which the chemical structure of cis-resveratrol is shown.
Figure 2:
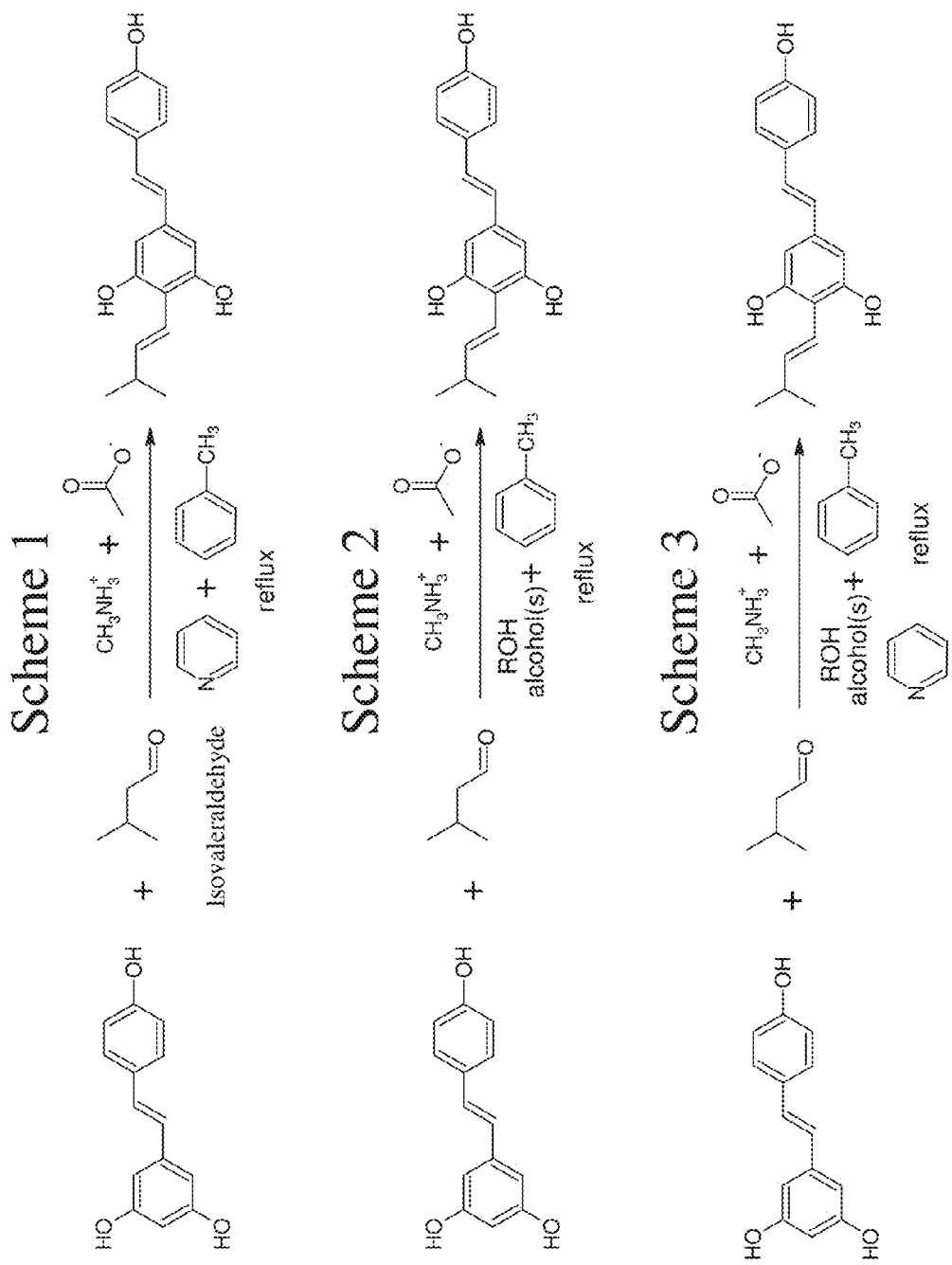
FIG. 2 is a diagram of embodiments of Schemes 1-3 comprising a chemical reaction of combining isovaleraldehyde and trans-resveratrol with a catalyst ($X_1$) and solvents ($Y_1$-$Y_3$).
Figure 3:
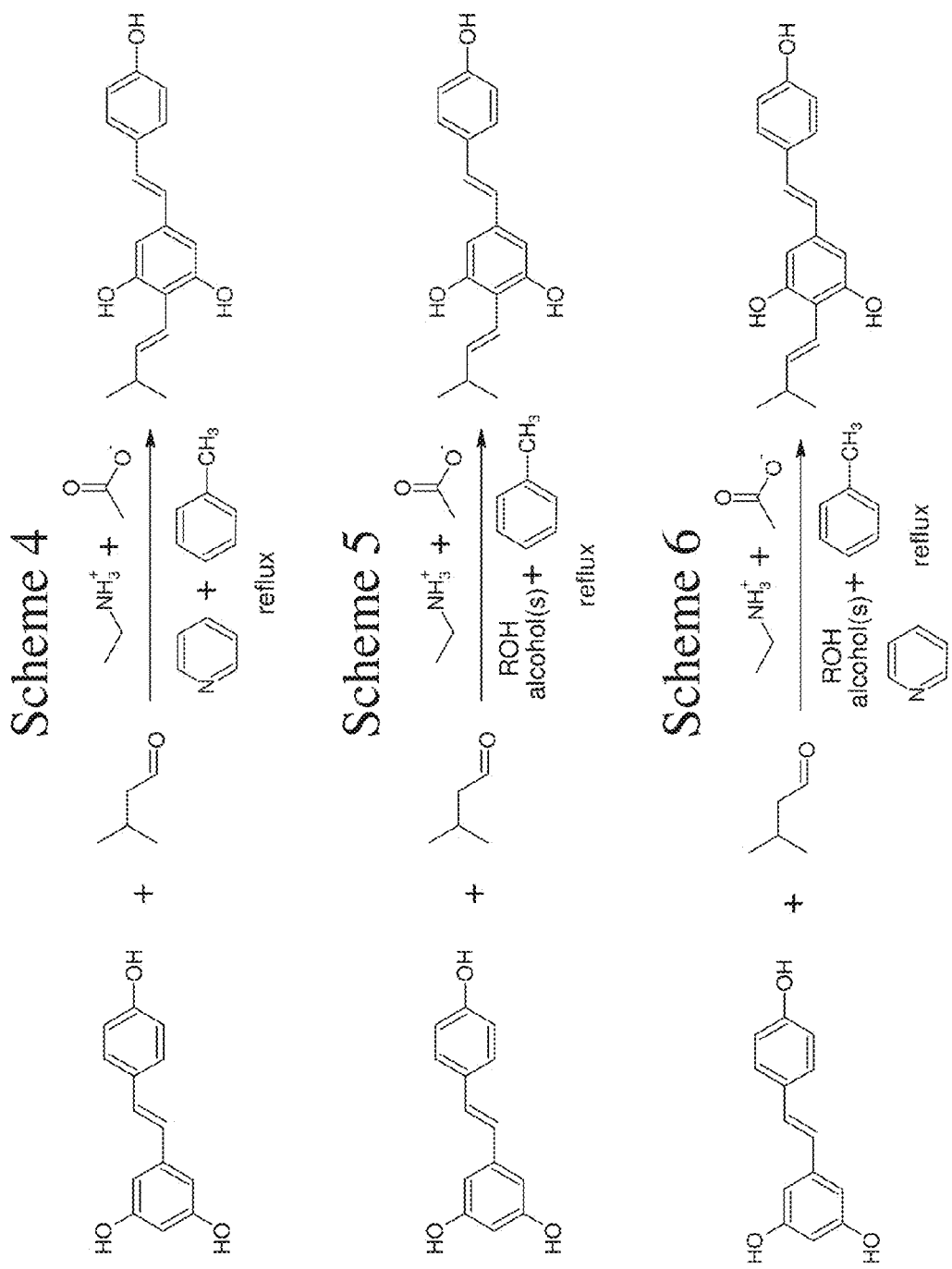
FIG. 3 is a diagram of embodiments of Schemes 4-6 comprising a chemical reaction of combining isovaleraldehyde and trans-resveratrol with a catalyst ($X_2$) and solvents ($Y_1$-$Y_3$).

FIGS. 1A through 1C are prior art diagrams showing chemical structures for the stilbenoids of the various embodiments disclosed herein. In FIG. 1A, the structure of trans-resveratrol is shown, wherein the trans refers to the double bond orientation connecting the two phenyl rings. The cis configuration (see FIG. 1C) is possible but the trans is regarded as the more efficacious compound, and the trans is used primarily in the methods disclosed herein. In FIG. 1B, the structure of trans-arachidin-3 is shown wherein the trans configuration still refers to the central double bond connecting the two phenyl rings. The added hydrocarbon chain is known to occur in nature and is called prenylation.

The embodiments disclosed herein comprise a single chemical reaction and a one pot method of producing synthetic, non-toxic trans-arachidin-3 from synthetic or naturally occurring trans-resveratrol. This method may be used in a large-scale manufacturing environment to economically produce FDA acceptable drinks, food, tablets, etc. comprising the synthetic trans-arachidin-3 for administration to mammals, such as humans, for a therapeutic benefit against a variety of diseases, disorders, and for generally promoting a healthy lifestyle.

Methods of Synthesizing Trans-Arachidin-3

FIGS. 2-21 illustrate various exemplary embodiments for the method of synthesizing trans-arachidin-3 as disclosed herein. Each embodiment, or "scheme", comprises reacting isovaleraldehyde with synthetic or naturally occurring trans-resveratrol. Isovaleraldehyde's IUPAC name is 3-methylbutyraldehyde, its systemic name is 3-methylbutanal, and its chemical formula is $(CH_3)_2CHCH_2CHO$. It is also an F.D.A. approved common food additive.

Catalyst (X)

The method of synthesizing further comprises a Catalyst (X) selected from the group consisting of: a mixture of primary alkylamines, a mixture of primary hydroxyalkyl amines, a mixture of carboxy amines (amino acids) with natural carboxylic acids (i.e. acetic acid), and any combination thereof. In an embodiment, the catalyst is selected from the group consisting of a mixture of a primary alkylamine with acetic acid, a mixture of a primary hydroxyalkyl amine with acetic acid, and carboxy amine.

As used herein, the terms "primary alkylamines", "mixtures of primary hydroxyalkyl amines", and "mixtures of carboxy amines (amino acids) with natural carboxylic acids (acetic acid)" are defined as per the understanding of one of skill in the art of chemistry.

Solvents (Y)

The solvent for use in the various embodiments comprise an organic solvent composed of an azeotropic toluene mixture comprising a liquid mixture of toluene with one or more other substances that retains the same composition in the vapor state as in the liquid state when distilled or partially evaporated under a certain pressure. The azeotropic toluene mixture has two roles of dissolving the highly polar resveratrol and to remove water from the reaction, which is a product of this one-step conversion. Non-limiting examples of suitable solvent pairs include azeotropic mixtures: $(Y_1)$ comprising toluene with pyridine: $(Y_2)$ comprising toluene with an alcohol ("R—OH") that forms an azeotrope with toluene; and, $(Y_3)$ comprising $((Y_1)+(Y_2))$. One skilled in the art could readily determine the relative amounts, concentrations, etc. of each component of the solvent's azeotropic toluene mixture without engaging in undue experimentation.

Azeotropic toluene and "R—OH" mixtures $(Y_2)$ suitable for use in the various embodiments comprise, by way of non-limiting examples: pyridine, n-butanol, n-propanol, 2-propanol, and 2-methyl-1-propanol.

Refluxing: As used herein, the term "refluxing" is defined as per the understanding of one of skill in the art of chemistry. In the various embodiments disclosed herein, the refluxing step of the composition occurs in a vessel. In an embodiment, the refluxing is carried out for about 24 hours at about, or between, 100-105 degrees Celsius; or alternatively at 105 degrees Celsius. It is understood that one skilled in the art could readily reflux the composition of resveratrol with the solvents and catalysts disclosed herein to produce arachidin-3 at alternative temperatures and durations.

Exemplary Solubility Experimentation and Solvent Selection

In one or more exemplary embodiments, selection and composition experiments were conducted to discover the most efficient solvent system in producing the highest purity and yield of trans-arachidin-3. Butanol, ethyl acetate, hexane, isopropanol, methanol, pyridine, and toluene were tested individually or as part of a system.

Toluene, an inexpensive food-grade solvent, was ineffective at dissolving trans-resveratrol alone. Scaling the setup to 5%, trans-resveratrol (0.0492 g) was added to a flask of toluene (10 mL), swirled, and heated. The solution appeared cloudy and particles were observed. The polarity of the solvent was too weak to dissolve the sample.

Experiments with pyridine had proven effective in driving the synthesis, so experiments to determine the minimum amount of pyridine required to dissolve trans-resveratrol were conducted. Solutions were prepared at 10, 20, and 30% pyridine/toluene, and the setup was scaled to 5%. After heating, the 10% system was completely dissolved; and the experiment was repeated using a 1, 2, 5, 6, 7 and 8% pyridine/toluene solution. The 6% binary solvent system was effective at dissolving trans-resveratrol with minimal heating and the experiment was duplicated to confirm.

1-Butanol was also effective in driving the synthesis and repeated reactions showed far fewer side products and qualitatively produced a higher yield, so experiments to minimize the amount of 1-butanol needed for trans-resveratrol dissolution were conducted. A 5, 10, 15, and 20% 1-butanol/toluene solutions were prepared, but all four were unsuccessful at dissolving trans-resveratrol. Solutions of 22, 25, and 27% 1-butanol/toluene were prepared and tested for solubility. Dissolution of trans-resveratrol occurred in the 25% flask with minimal heating and the experiment was duplicated to confirm.

Exemplary Schemes 1-60

The exemplary Schemes 1-60 in FIGS. 2-21 are carried out in a solvent $(Y_{1-3})$ using a catalyst $(X_{1-20})$ (See Table 1 for a disclosure of all compounds in the composition of each Scheme 1-60). It is noted that one of skill in the art could readily produce other similar schemes based on the disclosure herein and without having to engage in undue experimentation. The exemplary catalysts X1 is 1-amino-2-propanol in acetic acid.

TABLE 1

| Scheme | Reactants | Catalyst $(X_{1-20})$ | Solvent $(Y_{1-3})$ |
|---|---|---|---|
| 1 | isovaleraldehyde + trans-resveratrol | $X_1$ | $Y_1$ |
| 2 | isovaleraldehyde + trans-resveratrol | $X_1$ | $Y_2$ |
| 3 | isovaleraldehyde + trans-resveratrol | $X_1$ | $Y_3$ |
| 4 | isovaleraldehyde + trans-resveratrol | $X_2$ | $Y_1$ |
| 5 | isovaleraldehyde + trans-resveratrol | $X_2$ | $Y_2$ |
| 6 | isovaleraldehyde + trans-resveratrol | $X_2$ | $Y_3$ |
| 7 | isovaleraldehyde + trans-resveratrol | $X_3$ | $Y_1$ |
| 8 | isovaleraldehyde + trans-resveratrol | $X_3$ | $Y_2$ |
| 9 | isovaleraldehyde + trans-resveratrol | $X_3$ | $Y_3$ |
| 10 | isovaleraldehyde + trans-resveratrol | $X_4$ | $Y_1$ |
| 11 | isovaleraldehyde + trans-resveratrol | $X_4$ | $Y_2$ |
| 12 | isovaleraldehyde + trans-resveratrol | $X_4$ | $Y_3$ |
| 13 | isovaleraldehyde + trans-resveratrol | $X_5$ | $Y_1$ |
| 14 | isovaleraldehyde + trans-resveratrol | $X_5$ | $Y_2$ |
| 15 | isovaleraldehyde + trans-resveratrol | $X_5$ | $Y_3$ |
| 16 | isovaleraldehyde + trans-resveratrol | $X_6$ | $Y_1$ |
| 17 | isovaleraldehyde + trans-resveratrol | $X_6$ | $Y_2$ |
| 18 | isovaleraldehyde + trans-resveratrol | $X_6$ | $Y_3$ |
| 19 | isovaleraldehyde + trans-resveratrol | $X_7$ | $Y_1$ |
| 20 | isovaleraldehyde + trans-resveratrol | $X_7$ | $Y_2$ |
| 21 | isovaleraldehyde + trans-resveratrol | $X_7$ | $Y_3$ |
| 22 | isovaleraldehyde + trans-resveratrol | $X_8$ | $Y_1$ |
| 23 | isovaleraldehyde + trans-resveratrol | $X_8$ | $Y_2$ |
| 24 | isovaleraldehyde + trans-resveratrol | $X_8$ | $Y_3$ |
| 25 | isovaleraldehyde + trans-resveratrol | $X_9$ | $Y_1$ |
| 26 | isovaleraldehyde + trans-resveratrol | $X_9$ | $Y_2$ |
| 27 | isovaleraldehyde + trans-resveratrol | $X_9$ | $Y_3$ |
| 28 | isovaleraldehyde + trans-resveratrol | $X_{10}$ | $Y_1$ |
| 29 | isovaleraldehyde + trans-resveratrol | $X_{10}$ | $Y_2$ |
| 30 | isovaleraldehyde + trans-resveratrol | $X_{10}$ | $Y_3$ |
| 31 | isovaleraldehyde + trans-resveratrol | $X_{11}$ | $Y_1$ |
| 32 | isovaleraldehyde + trans-resveratrol | $X_{11}$ | $Y_2$ |
| 33 | isovaleraldehyde + trans-resveratrol | $X_{11}$ | $Y_3$ |
| 34 | isovaleraldehyde + trans-resveratrol | $X_{12}$ | $Y_1$ |
| 35 | isovaleraldehyde + trans-resveratrol | $X_{12}$ | $Y_2$ |
| 36 | isovaleraldehyde + trans-resveratrol | $X_{12}$ | $Y_3$ |
| 37 | isovaleraldehyde + trans-resveratrol | $X_{13}$ | $Y_1$ |
| 38 | isovaleraldehyde + trans-resveratrol | $X_{13}$ | $Y_2$ |

TABLE 1-continued

| Scheme | Reactants | Catalyst ($X_{1-20}$) | Solvent ($Y_{1-3}$) |
|---|---|---|---|
| 39 | isovaleraldehyde + trans-resveratrol | $X_{13}$ | $Y_3$ |
| 40 | isovaleraldehyde + trans-resveratrol | $X_{14}$ | $Y_1$ |
| 41 | isovaleraldehyde + trans-resveratrol | $X_{14}$ | $Y_2$ |
| 42 | isovaleraldehyde + trans-resveratrol | $X_{14}$ | $Y_3$ |
| 43 | isovaleraldehyde + trans-resveratrol | $X_{15}$ | $Y_1$ |
| 44 | isovaleraldehyde + trans-resveratrol | $X_{15}$ | $Y_2$ |
| 45 | isovaleraldehyde + trans-resveratrol | $X_{15}$ | $Y_3$ |
| 46 | isovaleraldehyde + trans-resveratrol | $X_{16}$ | $Y_1$ |
| 47 | isovaleraldehyde + trans-resveratrol | $X_{16}$ | $Y_2$ |
| 48 | isovaleraldehyde + trans-resveratrol | $X_{16}$ | $Y_3$ |
| 49 | isovaleraldehyde + trans-resveratrol | $X_{17}$ | $Y_1$ |
| 50 | isovaleraldehyde + trans-resveratrol | $X_{17}$ | $Y_2$ |
| 51 | isovaleraldehyde + trans-resveratrol | $X_{17}$ | $Y_3$ |
| 52 | isovaleraldehyde + trans-resveratrol | $X_{18}$ | $Y_1$ |
| 53 | isovaleraldehyde + trans-resveratrol | $X_{18}$ | $Y_2$ |
| 54 | isovaleraldehyde + trans-resveratrol | $X_{18}$ | $Y_3$ |
| 55 | isovaleraldehyde + trans-resveratrol | $X_{19}$ | $Y_1$ |
| 56 | isovaleraldehyde + trans-resveratrol | $X_{19}$ | $Y_2$ |
| 57 | isovaleraldehyde + trans-resveratrol | $X_{19}$ | $Y_3$ |
| 58 | isovaleraldehyde + trans-resveratrol | $X_{20}$ | $Y_1$ |
| 59 | isovaleraldehyde + trans-resveratrol | $X_{20}$ | $Y_2$ |
| 60 | isovaleraldehyde + trans-resveratrol | $X_{20}$ | $Y_3$ |

Purification and Qualification Analysis Techniques

The methods of synthesis of the various embodiments disclosed herein further comprise purifying the trans-arachidin-3 by methods well known to the skilled artisan, such as: high purity using column chromatography (neutral); high performance liquid chromatography (HPLC); high performance counter-current chromatography; thin layer chromatography (TLC), nuclear magnetic resonance spectroscopy (NMR); and infrared spectroscopy (IR).

With all of the exemplary experiments disclosed herein, analytical TLC using Macherey-Nagel POLYGRAM SIL G/UV254 pre-coated TLC-sheets were used to qualitatively determine the purity of products. An Entela certified, Mineralight Lamp model UVGL-58 multiband UV 254/366 was used to interpret TLC plates. Standard laboratory atmospheric conditions were observed; however, light was shielded from the still pot vessel during refluxing and exposure limited throughout the experiment.

Distillation of any solvent was performed with a Shaghai Ya Rong Rotary Evaporator, model RE-52CS-1, and all reactions used a Dean-Stark apparatus with a sand bath. Separation was performed via column chromatography (CC) using silica gel (ultrapure, 60-200 μm, Arcos Organics) and aluminum oxide (neutral, Brockmann I, 50-200 μm, Arcos Organics) with the latter providing less degradation. Multiple combinations and compositions of the mobile phase were tested. Post column chromatography, qualitative analysis was performed with a Shimadzu LC-20AD Liquid Chromatograph, SIL-10AF Auto Sampler, CTO-10AS Column Oven operating at (temperature), and a Spectra-Physics UV150 detector monitoring a specified wavelength. The instrument implemented an Atlantis Prep T3 (5.0 μm, 10 mm×250 mm) column with a guard column.

Exemplary Synthesis Procedure for Scheme 2

Materials and Methods

One of skill in the art would readily be able to synthesize the compositions of Schemes 1, 3-60, and the like, based upon the following disclosure of the method of synthesizing Scheme 2. Trans-Resveratrol (1.000 g, 0.00438 mol, MW 228.24 g·mol-1) was weighed and placed into a 250 milliliter round-bottom flask. Then 200 milliliters of the solvent of Scheme 1 comprising 27% n-butanol/toluene was added to the flask, and the flask was swirled for several seconds until dissolution of the trans-resveratrol. The reactant isovaleraldehyde (i.e. 3-methylbutyraldehyde) was then pipetted into the flask (500 μL, ≥0.00438 mol, 86.13 g·mol-1) and boiling chips (1 g) were added to the flask to reduce/prevent bumping. Next, the catalyst, DL-1-amino-2-propanol in acetic acid (2.01 mL, 0.1186 g·mL-1), was injected prior to attaching the vessel to a Dean-Stark apparatus. The solution was refluxed for 24 hours while maintaining it at a temperature of 105 degrees Celsius. The solution was then allowed to cool to room temperature while shielding it from any direct source of light. Thin layer chromatography (TLC) was used to determine reaction completion before performing the extraction step.

Two Liquid-Liquid extractions were performed in a 500 milliliter separatory funnel. The sample was washed with deionized (DI) water, and then the organic layer was extracted with a saturated sodium chloride (NaCl) solution. The organic layer was transferred to a 500 milliliter Erlenmeyer flask and dried over magnesium sulfate anhydrous or calcium chloride. The solution was left to rest before decanting into a 250 milliliter round bottom flask and concentrated under reduced pressure.

The residue was dissolved with 3 to 4 milliliters of the mobile phase and column chromatography was performed. Isolation of the trans-arachidin-3 target compound was verified with thin layer chromatography (TLC) plates before performing final separation with high performance liquid chromatography (HPLC).

HPLC: the trans-arachidin-3 sample was prepared for HPLC and the oven allowed to bring the column to 40 degrees Celsius. The UV-VIS detector was set to a wavelength of 330 nm; and using a methanol/DI water mobile phase, 50 μL was injected at a flow rate of 5 mL·min-1. Using a 60% methanol/DI water mobile phase, the trans-arachidin-3 sample was collected having a corresponding peak to the experimental HPLC chromatogram at 13.8 minutes. The trans-arachidin-3 sample fluoresced and was detected using a UV lamp. Thin layer chromatography (TLC) protocol was then used to validate the identity of the trans-arachidin-3 sample and compare it with the accepted trans-arachidin-3 values.

Figure 24:
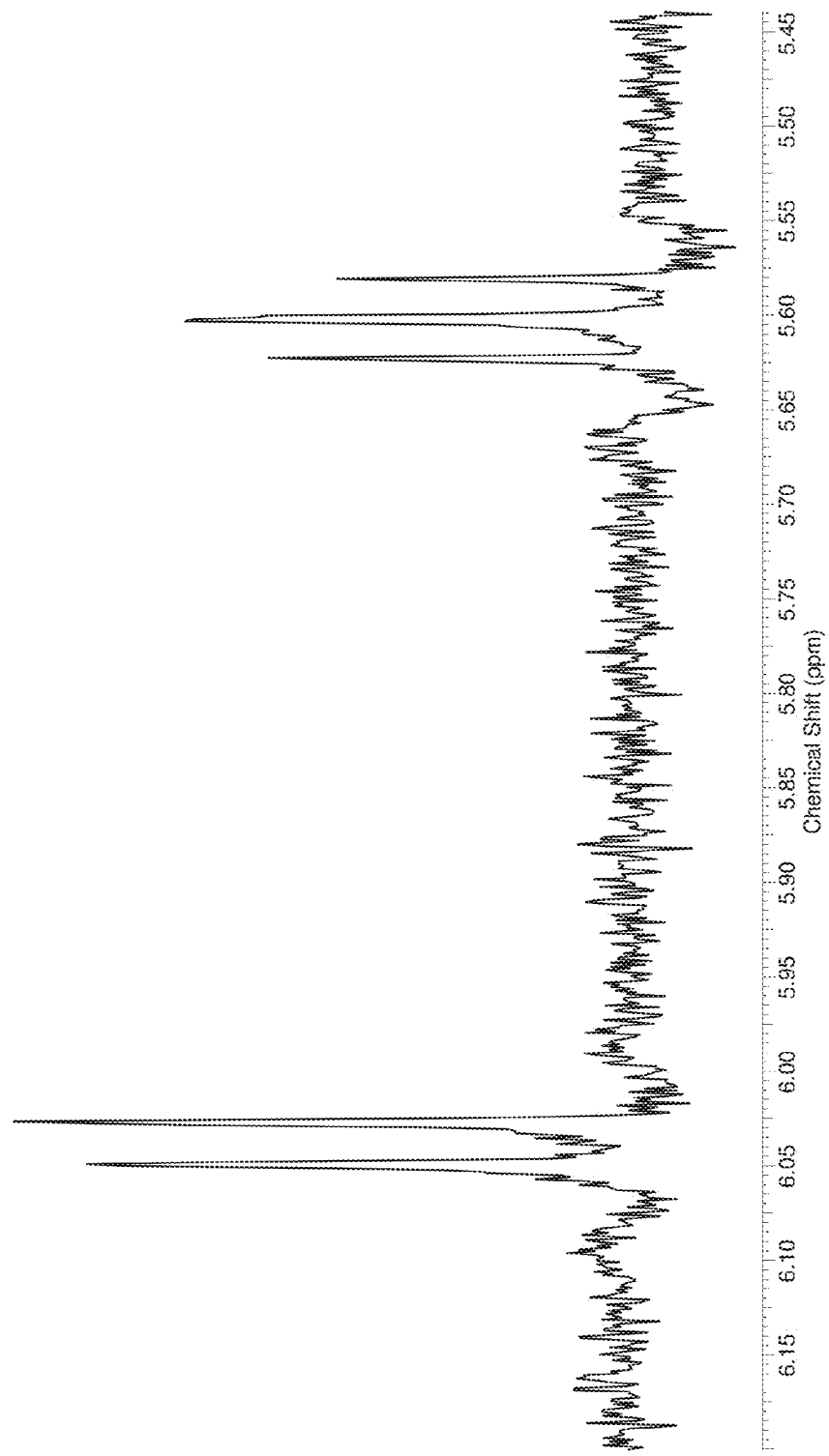
FIG. 24 is another diagram of trans-arachidin-3 $^1$H NMR Spectrum comprising a magnified view of FIG. 22 from about 6.2 ppm to 5.45 ppm.
Figure 25:
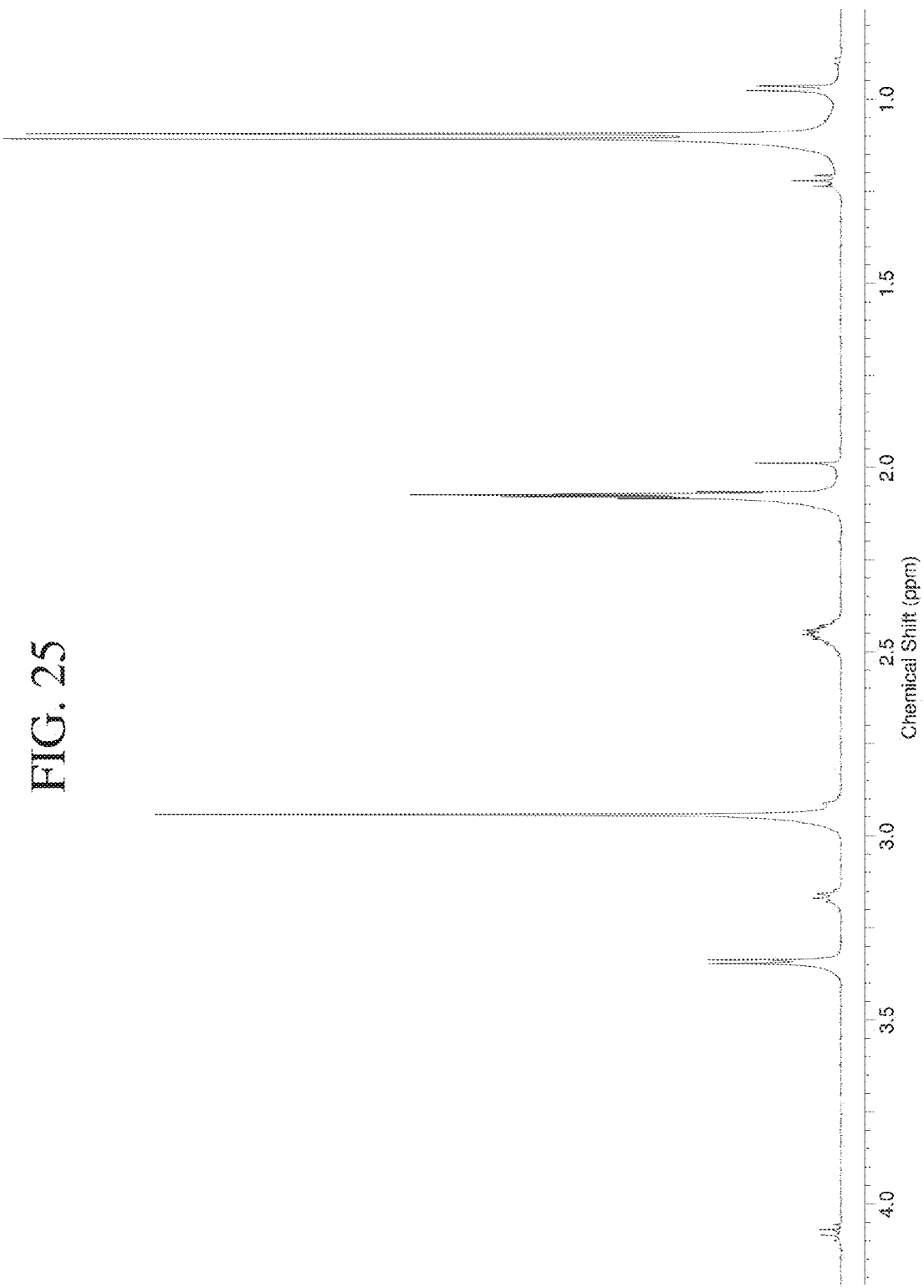
FIG. 25 is another diagram of trans-arachidin-3 $^1$H NMR Spectrum comprising a magnified view of FIG. 22 from about 4.1 ppm to 1.0 ppm.

A comparison of data from NMR and other spectroscopic methods against trans-arachidin-3 values found in the figures was conducted to further confirm synthesis (see FIGS. 22-30). Spectra were obtained on a Varian Unity 500 MHz NMR Spectrometer, yielding the following data for the purified trans-arachidin-3 (FIGS. 22-25): $^1$H NMR (500 MHz, acetone-$d_6$) δ 8.46 (1H, s), 8.31 (2H, s), 7.41 (2H, d, J=8.5 Hz), 6.96 (1H, d, J=16.3 Hz), 6.88-6.82 (3H, m), 6.63 (2H, s), 6.04 (1H, d, J=11.2 Hz), 5.60 (1H, t, J=10.6 Hz), 2.52-2.39 (1H, m), 1.10 (6H, d, J=6.7 Hz). Several features of the data suggested that this data represented trans-arachidin-3. No singlet appeared at 6.29 ppm for H4 on resveratrol (data not shown). In addition, features of the isoprenyl chain are present including a doublet at 1.10 ppm (6H), multiplet at 2.52-2.34 ppm (1H), and two distinctive peaks for an alkene at 5.60 ppm (1H) and 6.04 ppm (1H). FIG. 24 shows the two peaks at 5.60 and 6.04 ppm closer. The coupling constant of 11 Hz indicates a possible trans stereochemistry rather than a cis, which normally has a much smaller coupling constant, and the doublet and triplet is consistent with the n+1 rule for splitting at the unsaturated C1" and C2" positions, respectively. The solvent peak was acetone-$d_6$ (δ 2.1) and possible contaminants, including ethyl acetate (δ 4.1, q; 2.0, s; 1.2, t) and other unidentified molecule(s) with peaks at δ 7.7, 6.7, 3.3, 3.2, 2.9, and 1.0. Several of these peaks also appear in the literature (see Park, B. H., et. al. "Total Synthesis of Chiricanine A, Arahypin-1, trans-Arachidin-2, trans-Arachidin-3, and Arahypin-5 from Peanut Seeds," *Journal of Natural Products*, 2011, 74:644-649).

Figure 26:
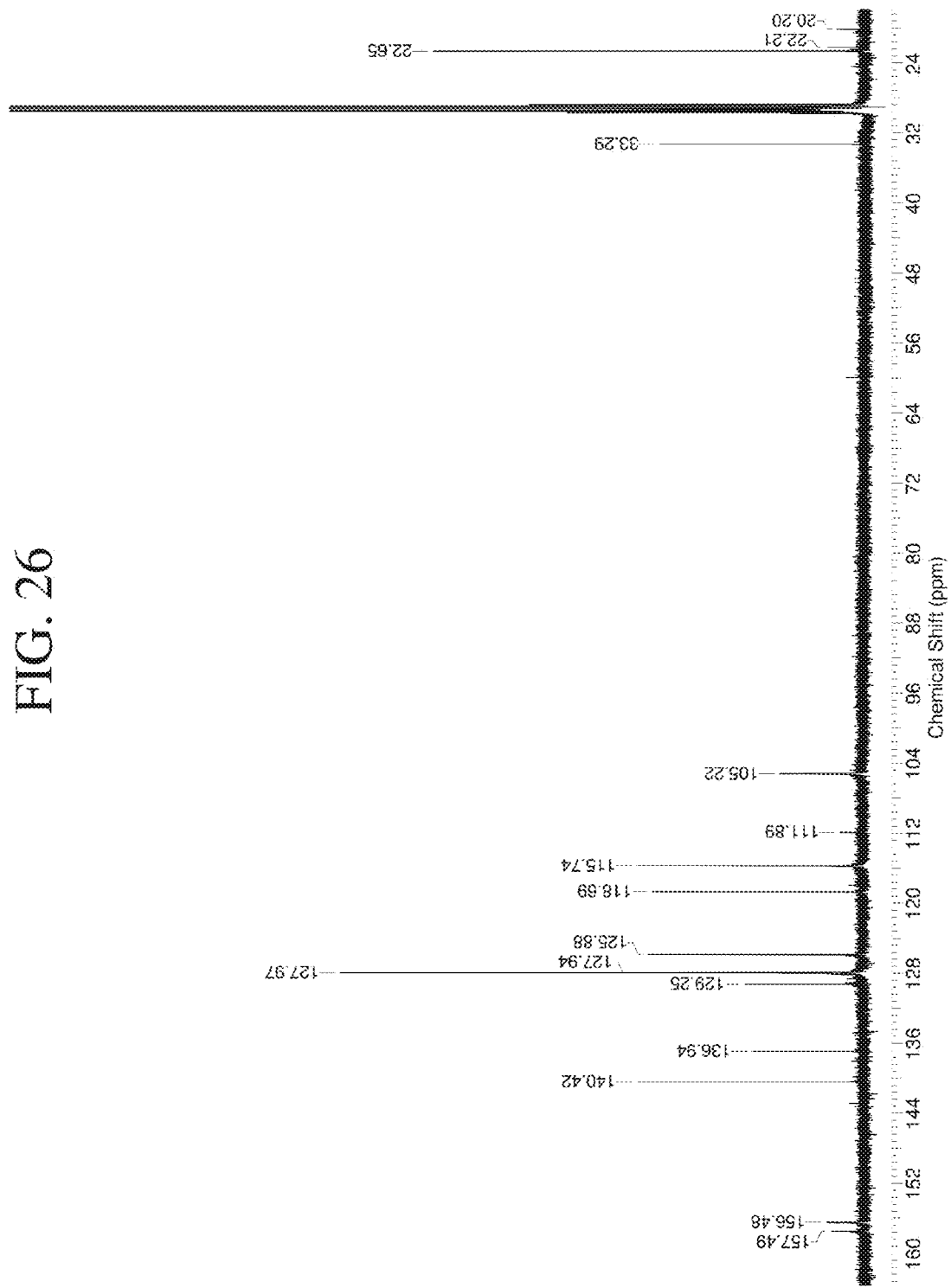
FIG. 26 is a diagram of the synthetic, non-toxic trans-arachidin-3 $^{13}$C NMR Spectrum.

FIG. 26 shows the $^{13}$C NMR spectrum for trans-arachidin-3: $^{13}$C NMR (125 MHz, acetone-$d_6$) δ 157.5, 156.5, 140.4, 136.9, 129.3, 127.97, 127.94, 125.9, 118.7, 115.7, 111.9, 105.2, 33.3, 22.6. Key indications of the isoprenyl chain included the peaks at 22.6 ppm (C4"/C5") and 33.3 ppm (C3"). Furthermore, the chemical shift of 33.3 ppm suggests that this carbon is sp$^3$ hybridized and does not possess unsaturation, suggesting again unsaturation at C1" and C2" positions. Lastly, 14 peaks suggest 14 unique carbon atoms, 4 more peaks than resveratrol (10 signals; data not shown). Lastly, this $^{13}$C NMR spectrum was nearly identical to the chemical shift data provide in the research literature for trans-arachidin-3 see Park, B. H., et. al. "Total Synthesis of Chiricanine A, Arahypin-1, trans-Arachidin-2, trans-Arachidin-3, and Arahypin-5 from Peanut Seeds," *Journal of Natural Products*, 2011, 74:644-649; supplemental data).

Figure 27:
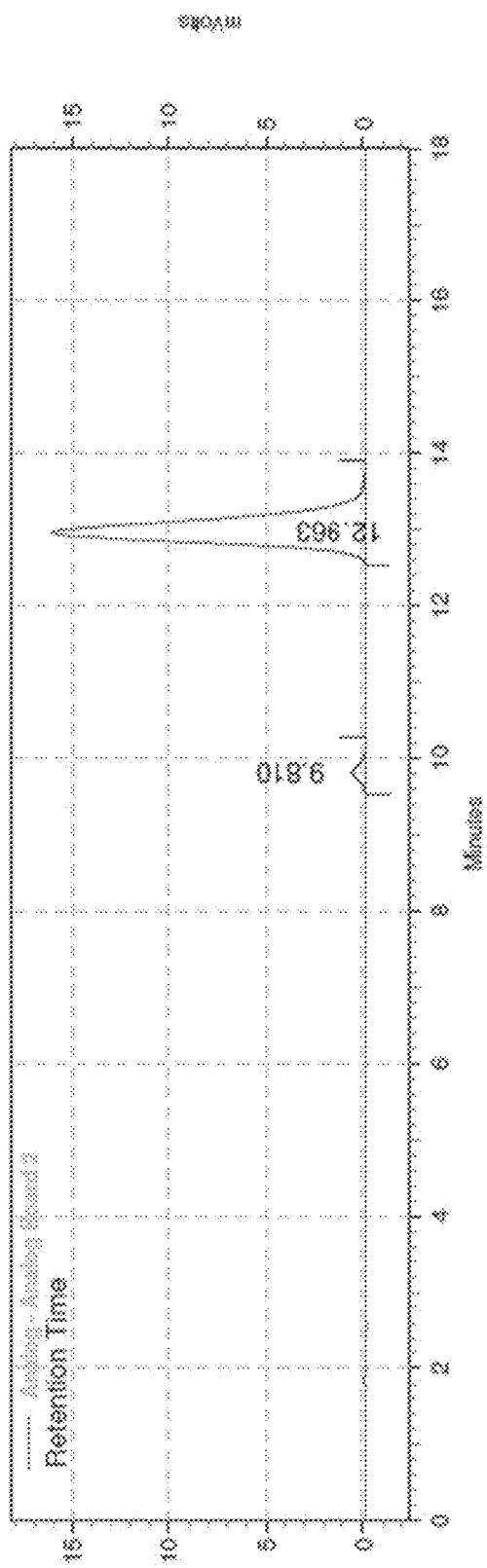
FIG. 27 is a HPLC Chromatogram of trans-arachidin-3 purified from peanut plant hairy root cultures
Figure 28:
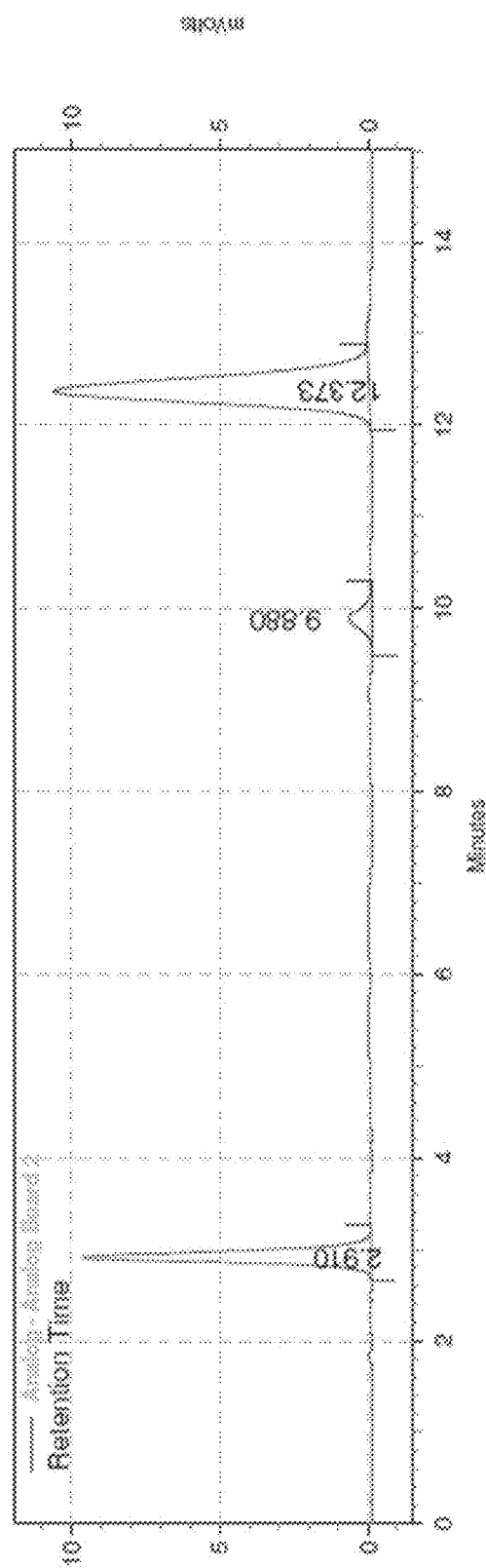
FIG. 28 is a diagram of an HPLC chromatogram of the synthetic, non-toxic trans-arachidin-3 with a peak for synthetic trans-arachidin-3 at 12.4 minutes versus FIG. 27's purified trans-arachidin-3 at 13.0 minutes.
Figure 29:
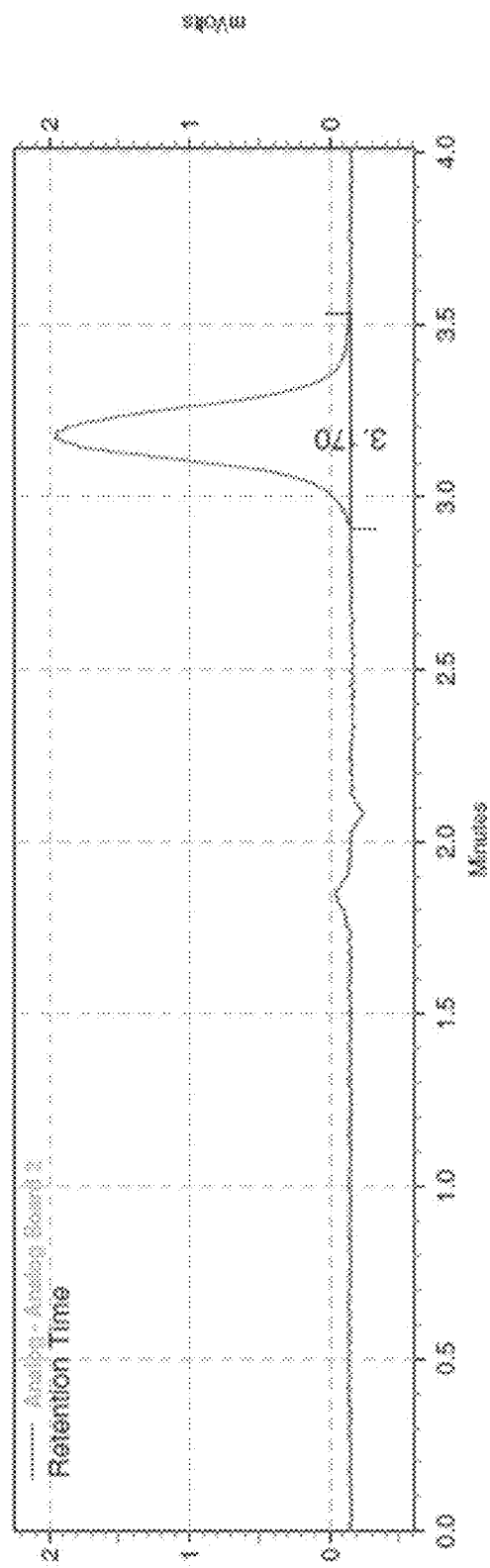
FIG. 29 is a diagram of an HPLC chromatogram of the synthetic, non-toxic trans-arachidin-3 with a peak at 2.9 for the unreacted trans-resveratrol.
Figure 30:
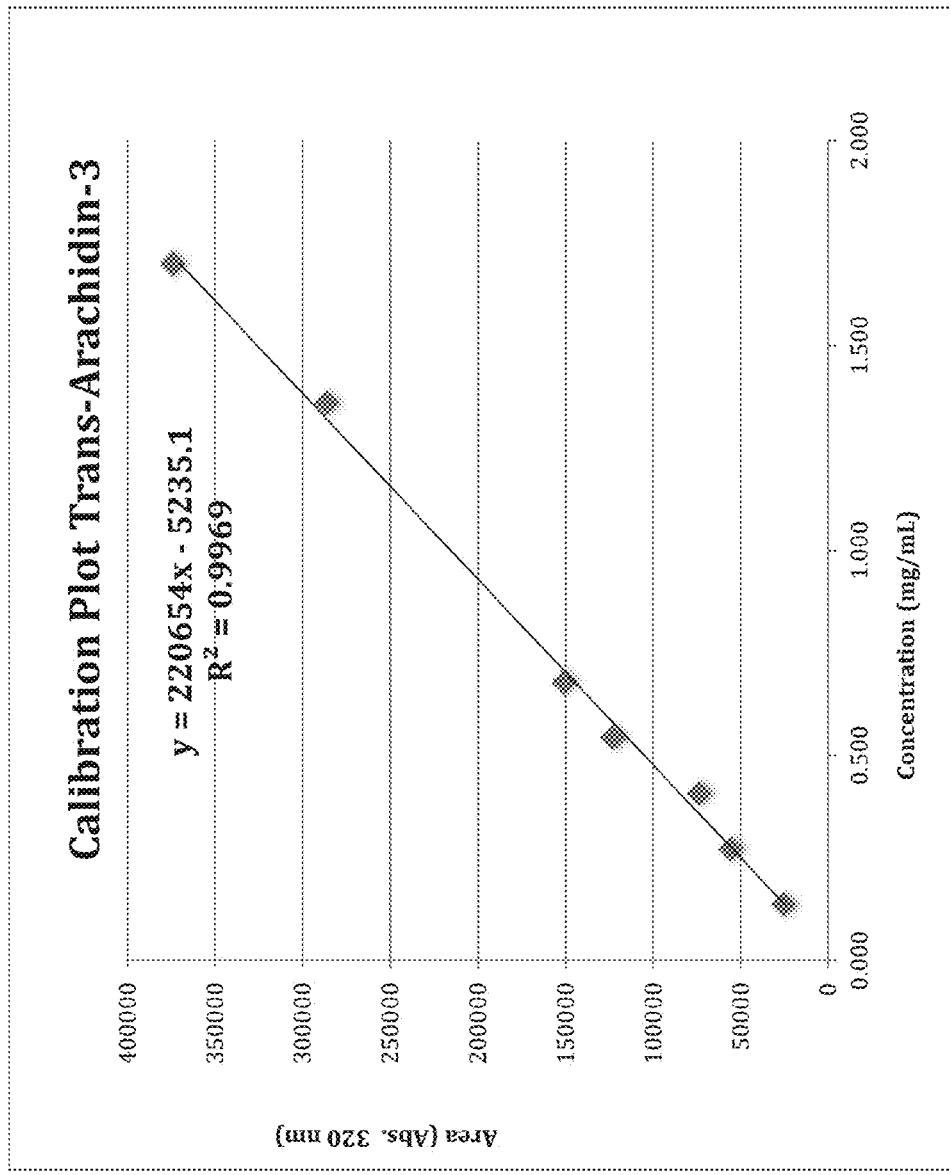
FIG. 30 is a diagram of a calibration plot of trans-arachidin-3 to estimate the concentration of a sample of synthetically produced trans-arachidin-3.

FIG. 27 shows the prior art HPLC Chromatogram of trans-arachidin-3 purified from peanut plant hairy root cultures (also see U.S. Patent Application 20100130623 A1, to Medina-Bolivar et al, filed Dec. 15, 2009, the entirety of which are hereby incorporated by reference). The peak with a retention time of 13.0 minutes corresponded to trans-arachidin-3. Using similar HPLC conditions, a crude reaction mixture containing trans-arachidin-3 resulted in FIG. 28 chromatogram. The peak at 12.4 minutes corresponded to trans-arachidin-3 within experimental error. The peak at 2.9 corresponded to unreacted trans-resveratrol; the standard for this molecule was provided (FIG. 29). Reaction yields for the provided Schemes 1-60 were determined using HPLC by first purifying a large quantity of trans-arachidin-3 and then varying the concentration of it in methanol or acetonitrile (1% acetic acid). In this way, a calibration plot was developed using 0.136-1.700 mg/ml trans-arachidin-3 and the peak area was plotted to estimate an equation of linearity using regression analysis (FIG. 30). This equation was then used in conjunction with the total peak area of the reaction crudes to estimate the relative amount of trans-arachidin-3. The equation determined through regression analysis to find a best fit line between the data points was y=220654x−5235. The correlation coefficient (R$^2$) of 0.997 indicated precision between the data points. To determine an unknown concentration, provide the HPLC peak area (variable y) obtained from a known volume, then solve for the variable x to obtain the estimate of concentration. The relative concentration was also obtained by comparing the peak area of trans-arachidin-3 to the other peaks corresponding to resveratrol and other unknown by-product(s).

Exemplary Synthesis Procedure for Scheme 9

Ethanol Amine Catalyst

Figure 4:
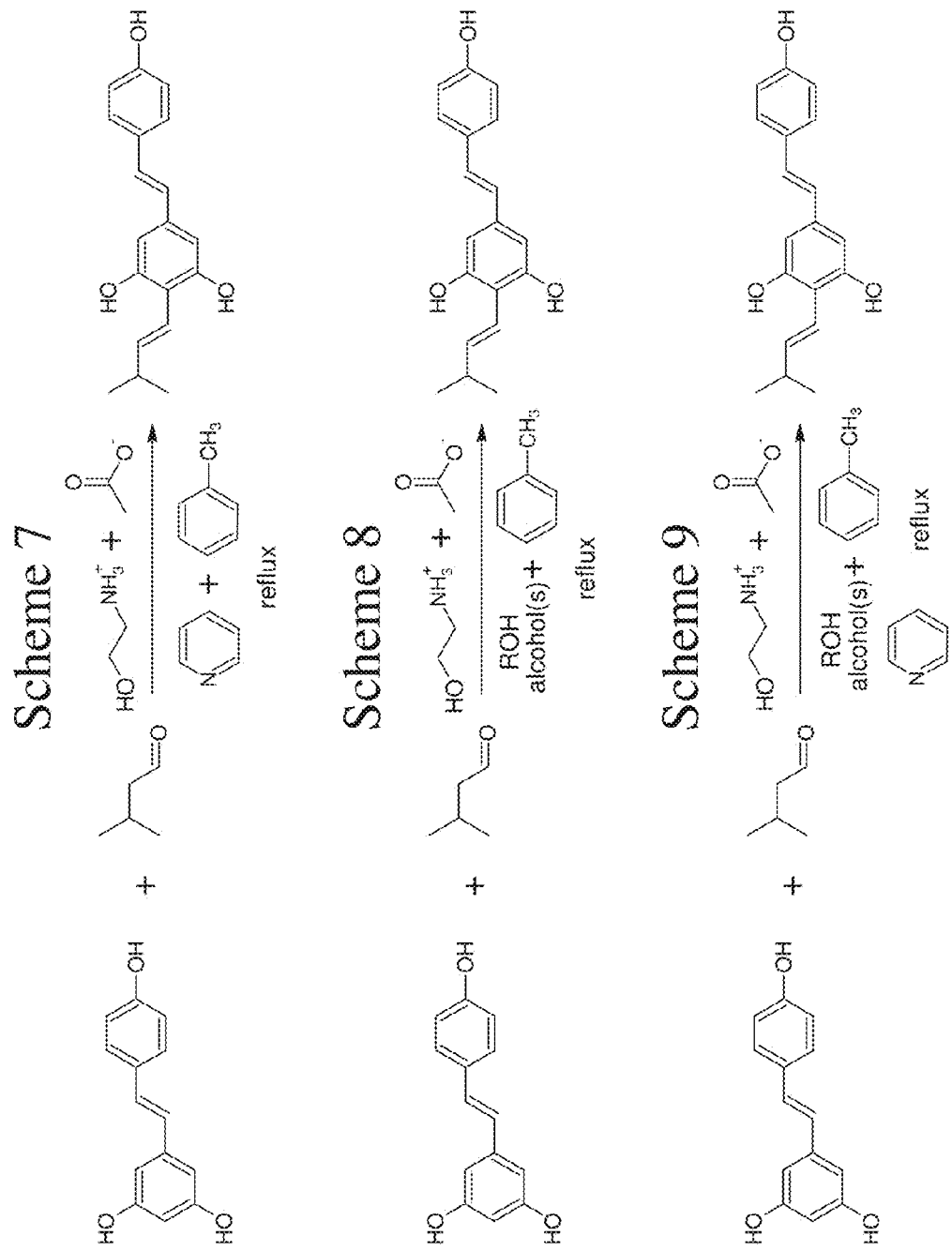
FIG. 4 is a diagram of embodiments of Schemes 7-9 comprising a chemical reaction of combining isovaleraldehyde and trans-resveratrol with a catalyst ($X_3$) and solvents ($Y_1$-$Y_3$).

The procedure for synthesizing Scheme 9 of FIG. 4 using an ethanol amine catalyst: Resveratrol (1.000 g, 0.00438 mol, MW 228.24 g·mol-1) was placed in a 250 mL round-bottom flask. To the flask was added: 136 mL of toluene, 54 mL of n-butanol, 10 mL of pyridine, and 10 mL of acetic acid, which was then swirl for several seconds to dissolve. 3-methylbutyraldehyde (1000 μL, 0.00438 mol, 86.13 g·mol-1) was pipetted into the flask, and then boiling chips (1 g) were added to prevent bumping. The catalyst, ethanol amine (0.500 mL, density 0.1186 g·mL-1) was then pipetted shortly before attaching the still pot to a Dean-Stark apparatus. The solution was then refluxed for 24 hours while maintaining a temperature of 100-105 degrees Celsius. Approximately, 1-2 mL of water was observed in the trap following the reaction. The solution was allowed to cool to room temperature, and then concentrated using a rotary evaporator. Thin layer chromatography and high performance liquid chromatography was used to determine the reaction yield. The reaction yield for this catalyst was 39.4% or 0.511 grams.

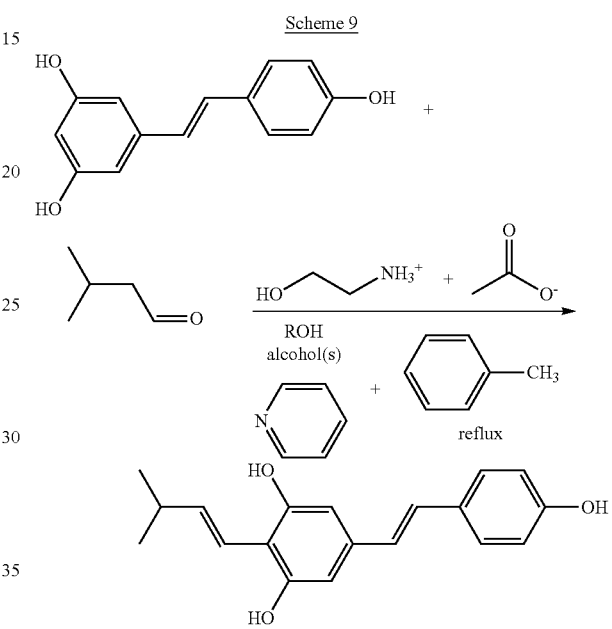

Scheme 9

Exemplary Synthesis Procedure for Scheme 12

1-Amino-2-Propanol Catalyst

Figure 5:
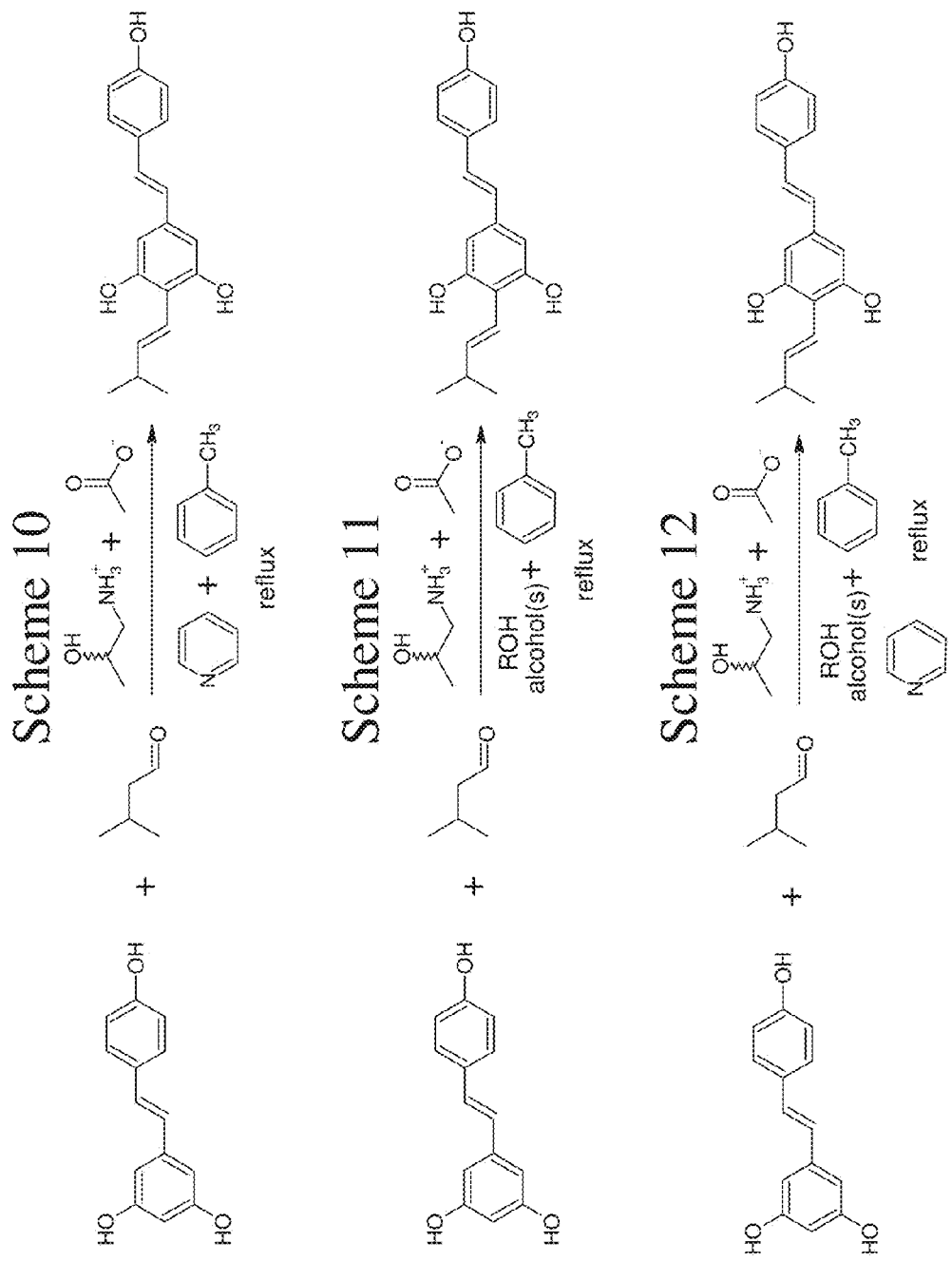
FIG. 5 is a diagram of embodiments of Schemes 10-12 comprising a chemical reaction of combining isovaleraldehyde and trans-resveratrol with a catalyst ($X_4$) and solvents ($Y_1$-$Y_3$).

The procedure for synthesizing Scheme 12 of FIG. 5 using a 1-amino-2-propanol catalyst are as follows. Resveratrol (1.000 g, 0.00438 mol, MW 228.24 g·mol-1) was placed in a 250 mL round-bottom flask. To the flask was added: 136 mL of toluene, 54 mL of n-butanol, 10 mL of pyridine, and 10 mL of acetic acid, which was then swirled for several seconds to dissolve. 3-methylbutyraldehyde (1000 μL, ≥0.00438 mol, 86.13 g·mol-1) was pipetted into the flask, and then boiling chips (1 g) were added to prevent bumping.

The catalyst, 1-amino-2-propanol (0.500 mL, density 0.973 g·mL-1) was then pipetted shortly before attaching the still pot to a Dean-Stark apparatus. The solution was then refluxed for 24 hours while maintaining a temperature of 100-103 degrees Celsius. Approximately, 1.8 mL of water was observed in the trap following the reaction. The solution was allowed to cool to room temperature, and then concentrated using a rotary evaporator. Thin layer chromatography and high performance liquid chromatography were used to determine the reaction yield. The reaction yield of trans-arachidin-3 for this catalyst was 79.8% or 1.036 grams.

13

Scheme 12

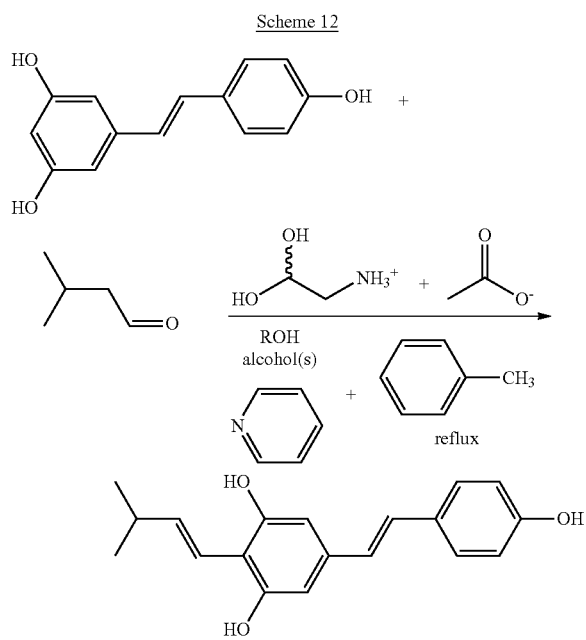

Exemplary Synthesis Procedure for Scheme 15 n-Propyl Amine Catalyst

Figure 6:
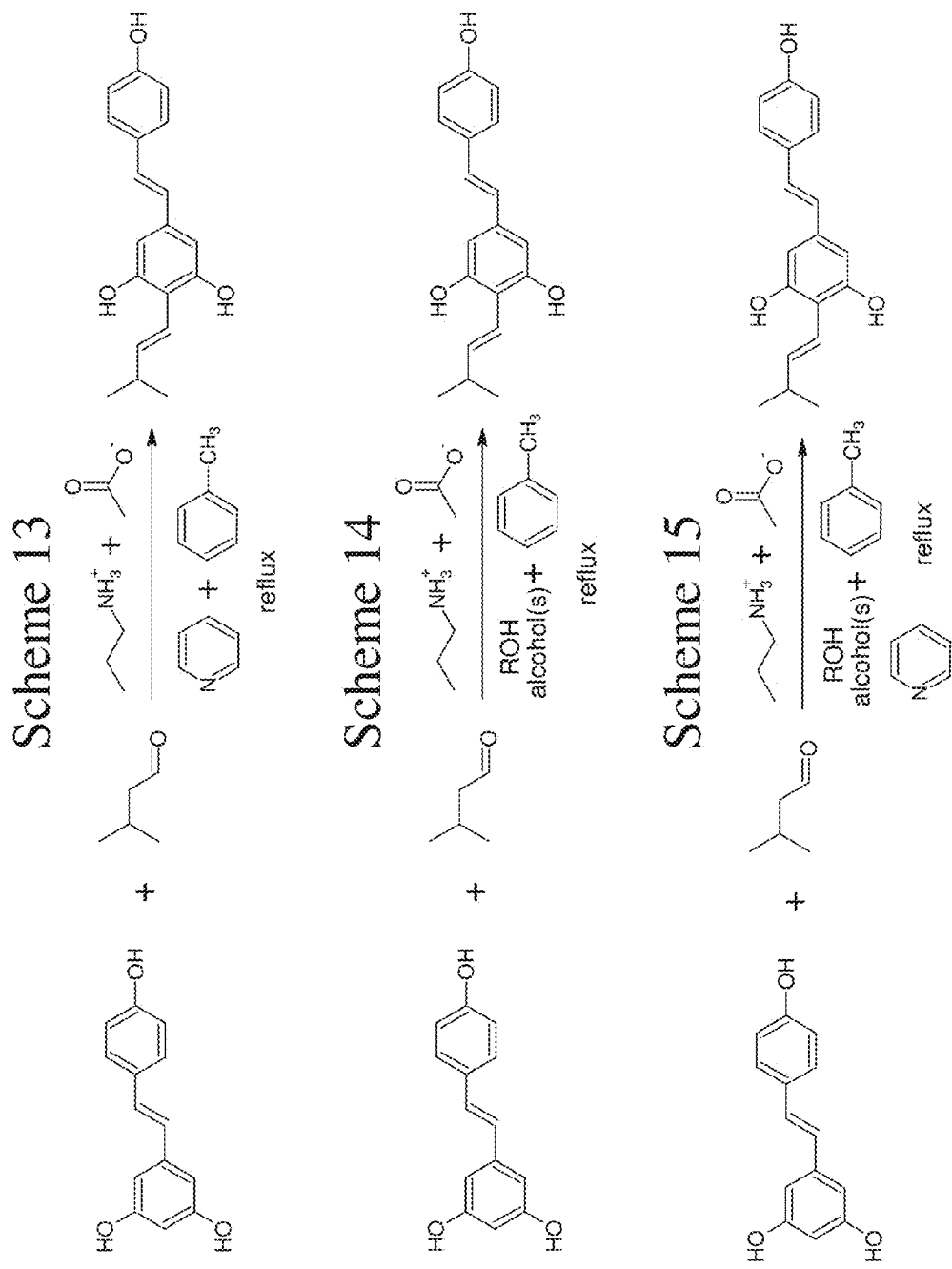
FIG. 6 is a diagram of embodiments of Schemes 13-15 comprising a chemical reaction of combining isovaleraldehyde and trans-resveratrol with a catalyst ($X_5$) and solvents ($Y_1$-$Y_3$).
Figure 7:
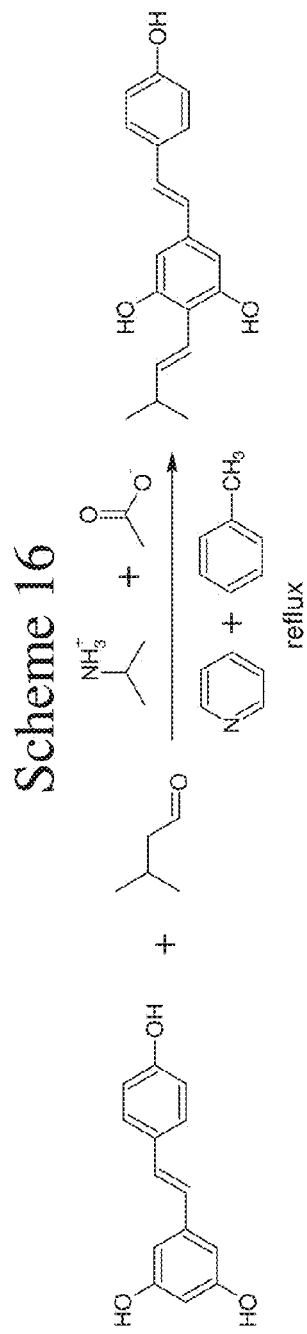
FIG. 7 is a diagram of embodiments of Schemes 16-18 comprising a chemical reaction of combining isovaleraldehyde and trans-resveratrol with a catalyst ($X_6$) and solvents ($Y_1$-$Y_3$).
Figure 7:
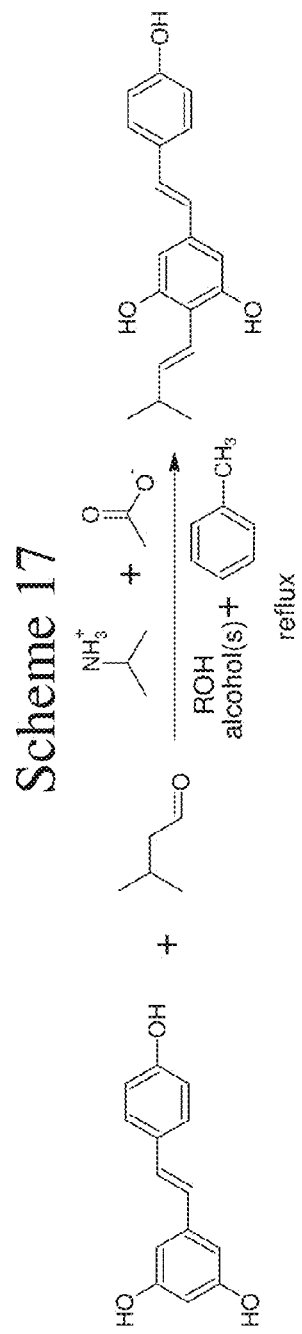
Figure 7:
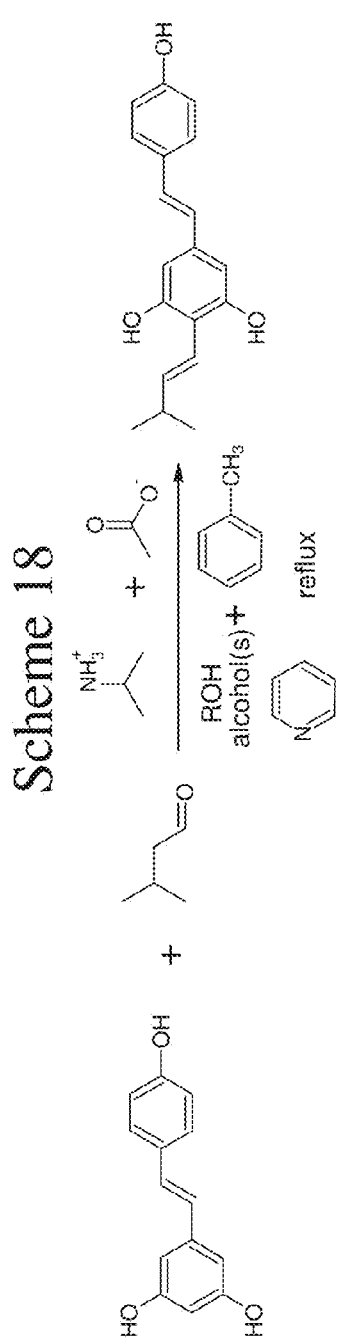
Figure 8:
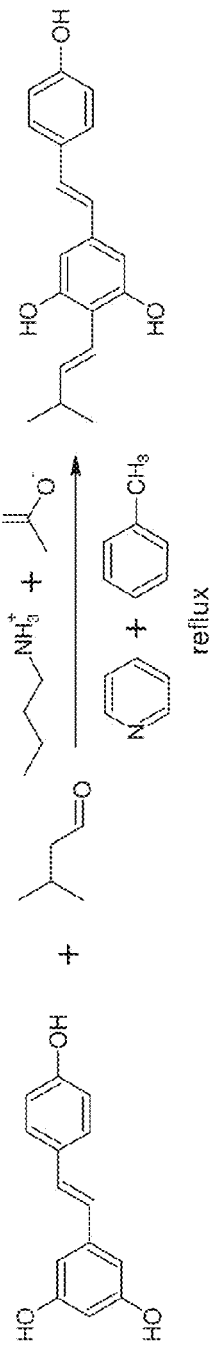
FIG. 8 is a diagram of embodiments of Schemes 19-21 comprising a chemical reaction of combining isovaleraldehyde and trans-resveratrol with a catalyst ($X_7$) and solvents ($Y_1$-$Y_3$).
Figure 8:
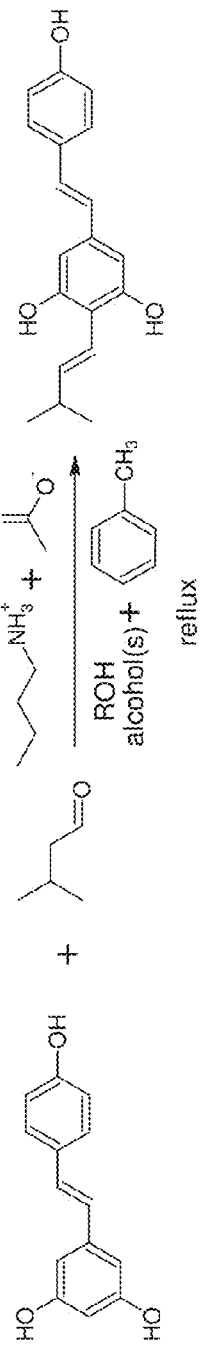
Figure 8:
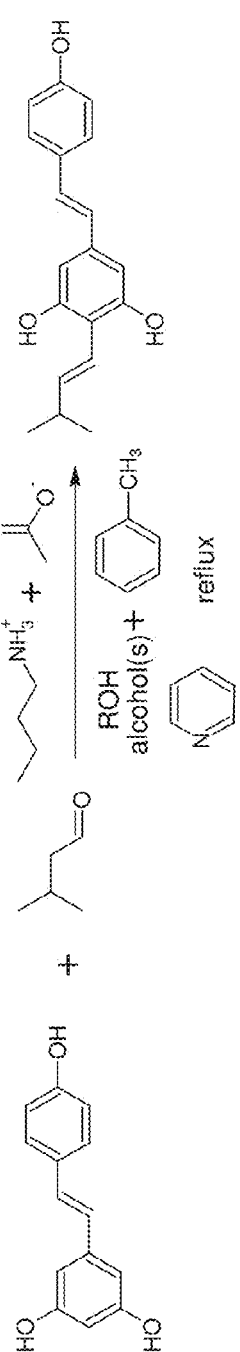
Figure 9:
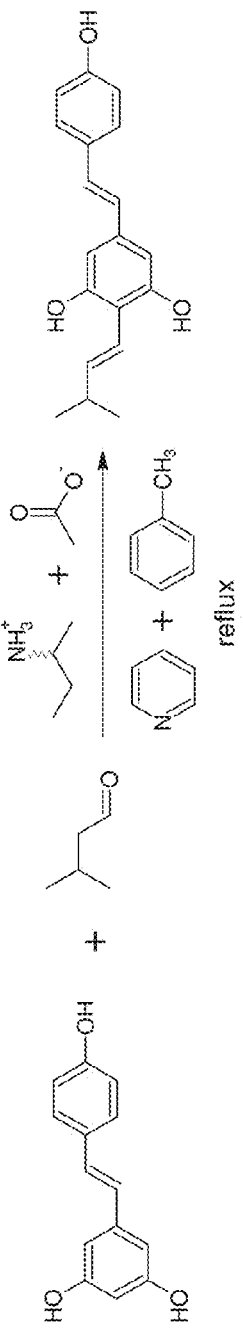
FIG. 9 is a diagram of embodiments of Schemes 22-24 comprising a chemical reaction of combining isovaleraldehyde and trans-resveratrol with a catalyst ($X_8$) and solvents ($Y_1$-$Y_3$).
Figure 9:
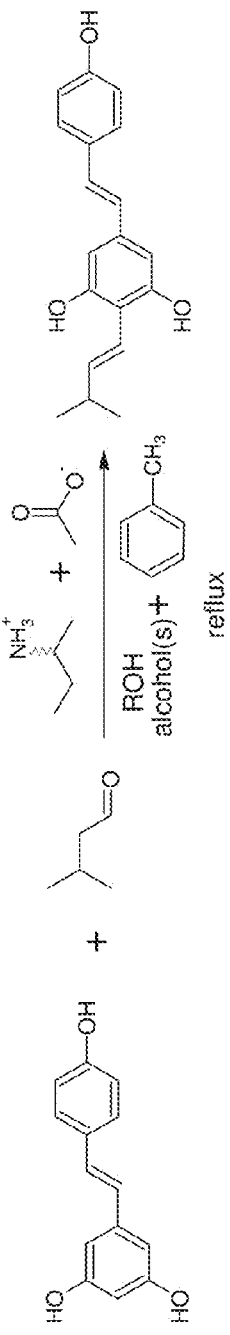
Figure 9:
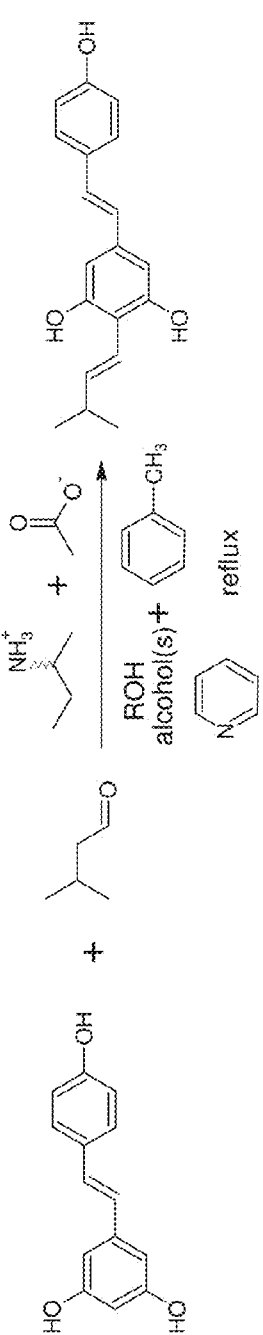
Figure 10:
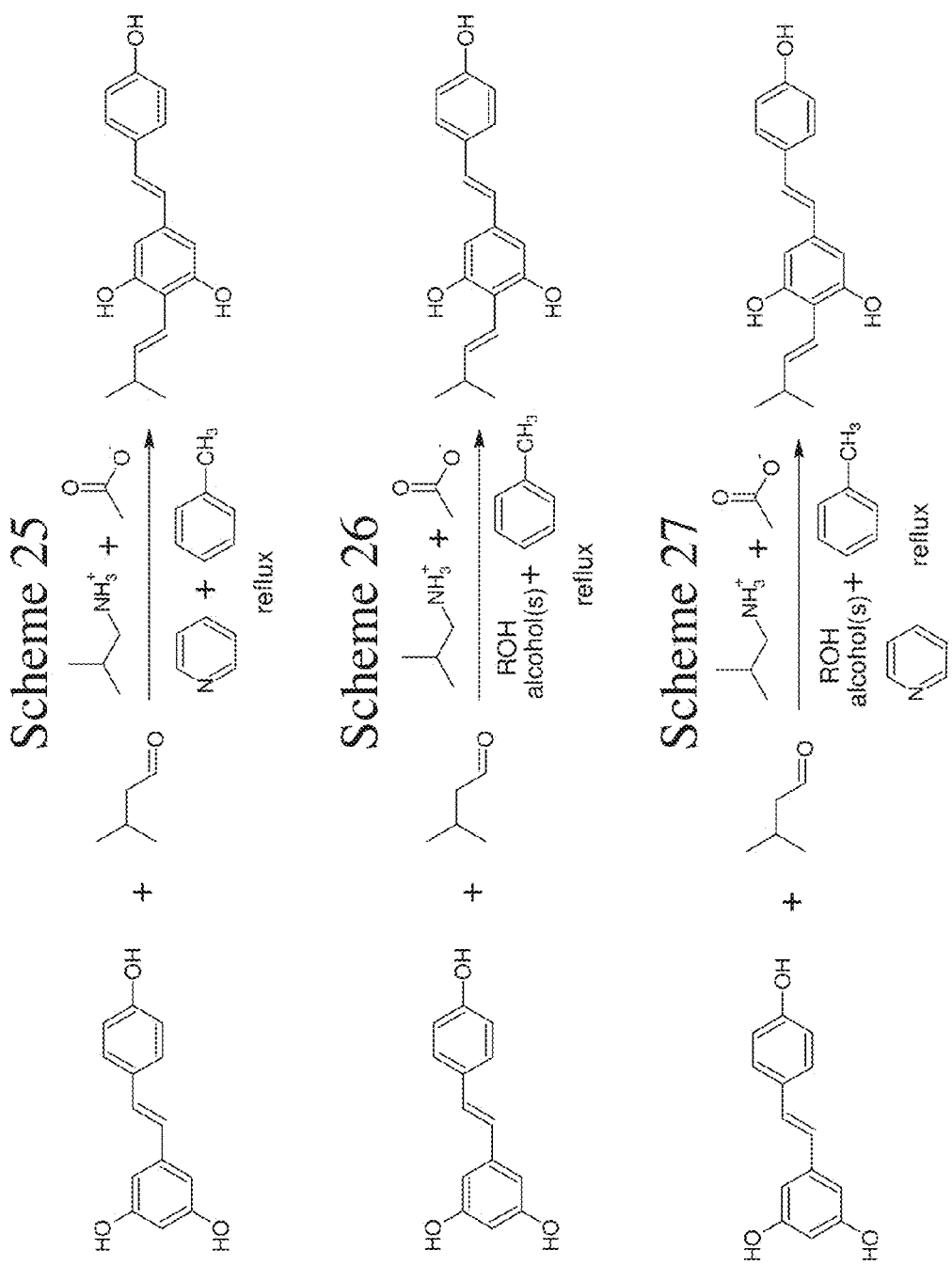
FIG. 10 is a diagram of embodiments of Schemes 25-27 comprising a chemical reaction of combining isovaleraldehyde and trans-resveratrol with a catalyst ($X_9$) and solvents ($Y_1$-$Y_3$).
Figure 11:
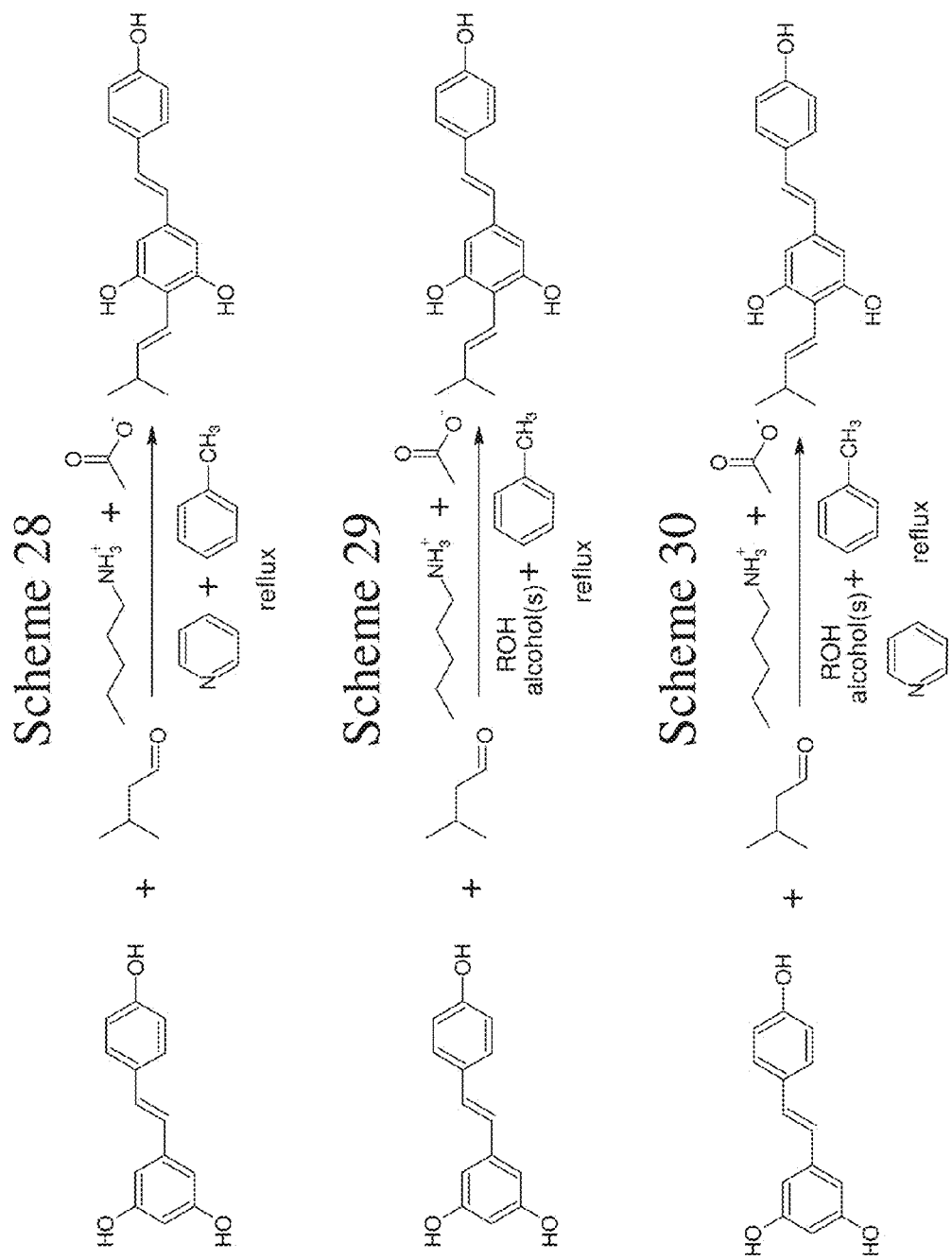
FIG. 11 is a diagram of embodiments of Schemes 28-30 comprising a chemical reaction of combining isovaleraldehyde and trans-resveratrol with a catalyst ($X_{10}$) and solvents ($Y_1$-$Y_3$).
Figure 12:
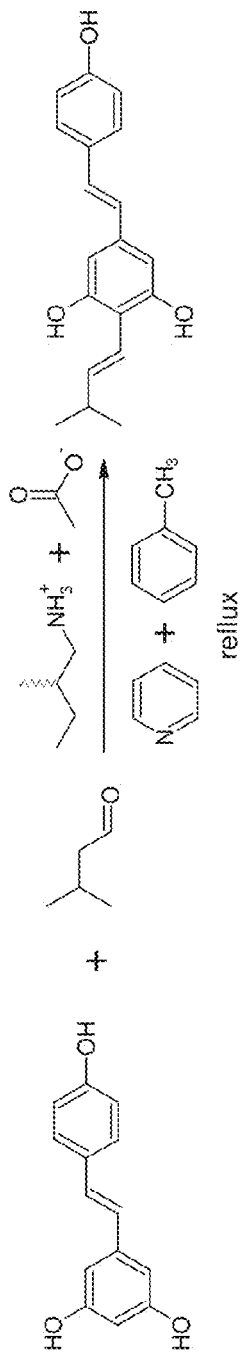
FIG. 12 is a diagram of embodiments of Schemes 31-33 comprising a chemical reaction of combining isovaleraldehyde and trans-resveratrol with a catalyst ($X_{11}$) and solvents ($Y_1$-$Y_3$).
Figure 12:
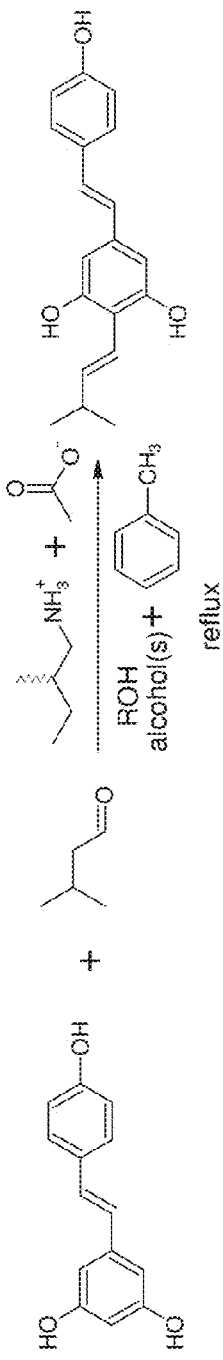
Figure 12:
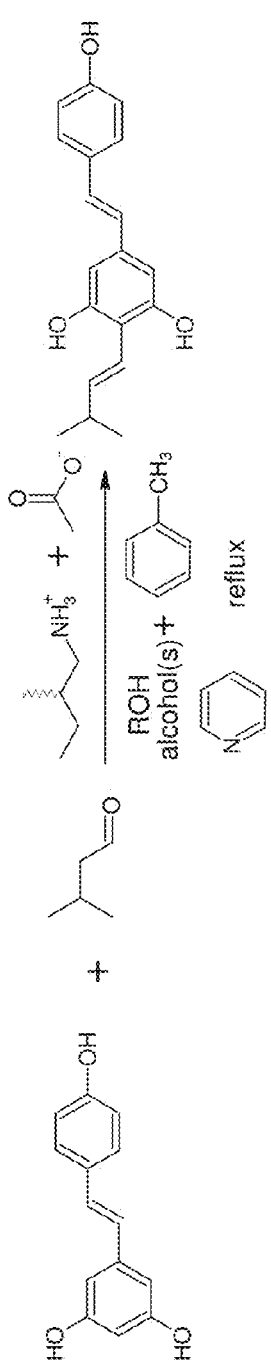
Figure 13:
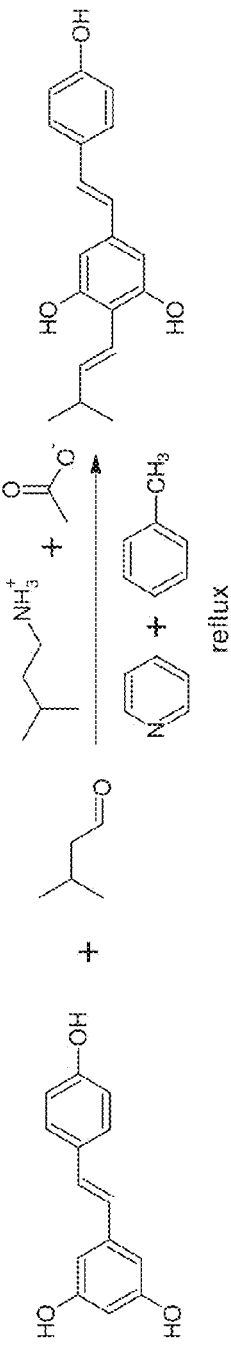
FIG. 13 is a diagram of embodiments of Schemes 34-36 comprising a chemical reaction of combining isovaleraldehyde and trans-resveratrol with a catalyst ($X_{12}$) and solvents ($Y_1$-$Y_3$).
Figure 13:
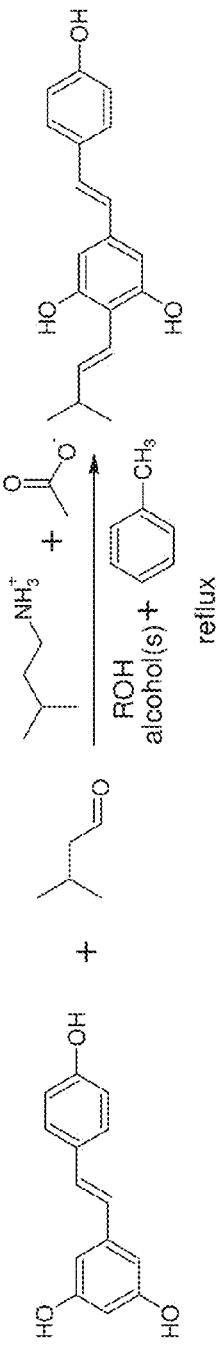
Figure 13:
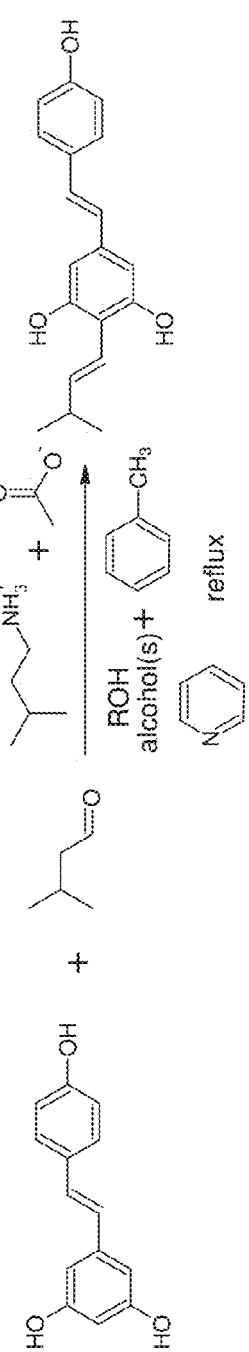
Figure 14:
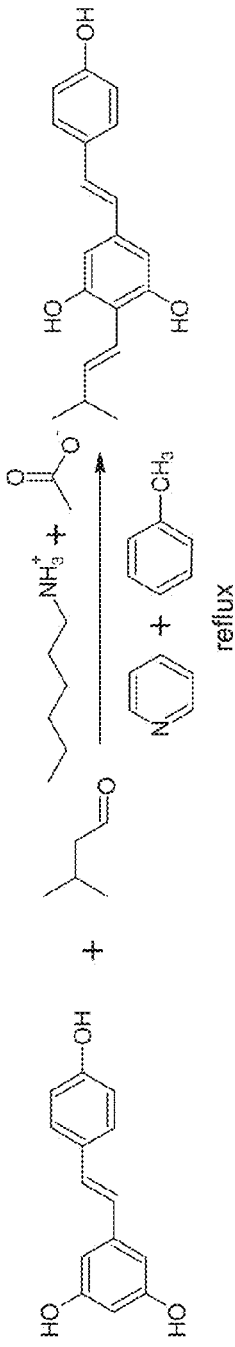
FIG. 14 is a diagram of embodiments of Schemes 37-39 comprising a chemical reaction of combining isovaleraldehyde and trans-resveratrol with a catalyst ($X_{13}$) and solvents ($Y_1$-$Y_3$).
Figure 14:
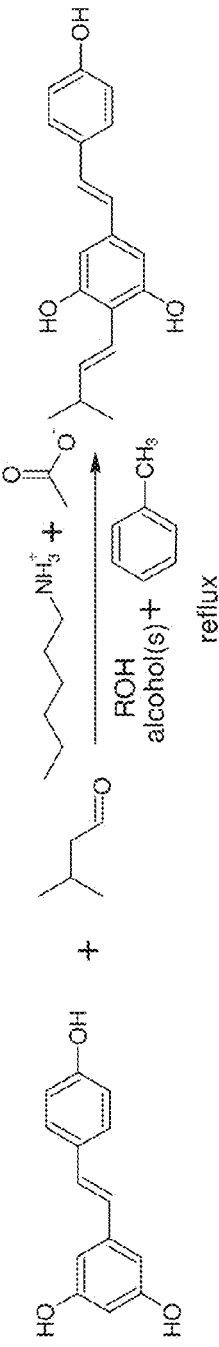
Figure 14:
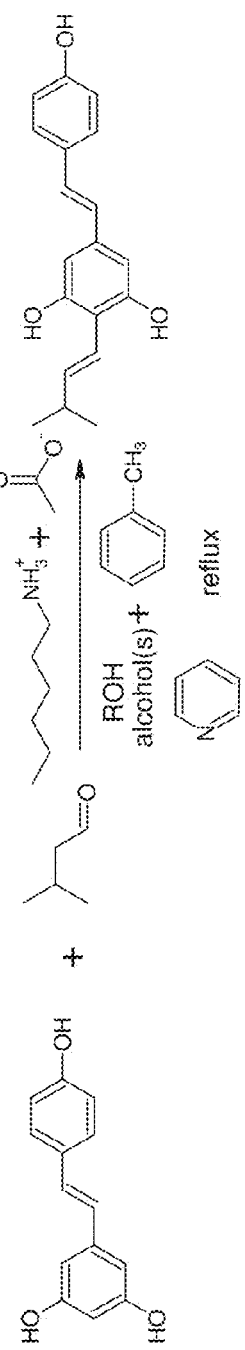
Figure 15:
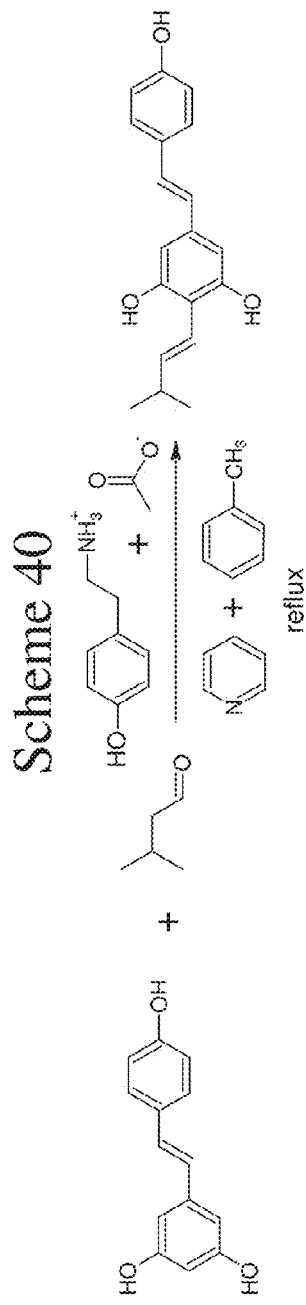
FIG. 15 is a diagram of embodiments of Schemes 40-42 comprising a chemical reaction of combining isovaleraldehyde and trans-resveratrol with a catalyst ($X_{14}$) and solvents ($Y_1$-$Y_3$).
Figure 15:
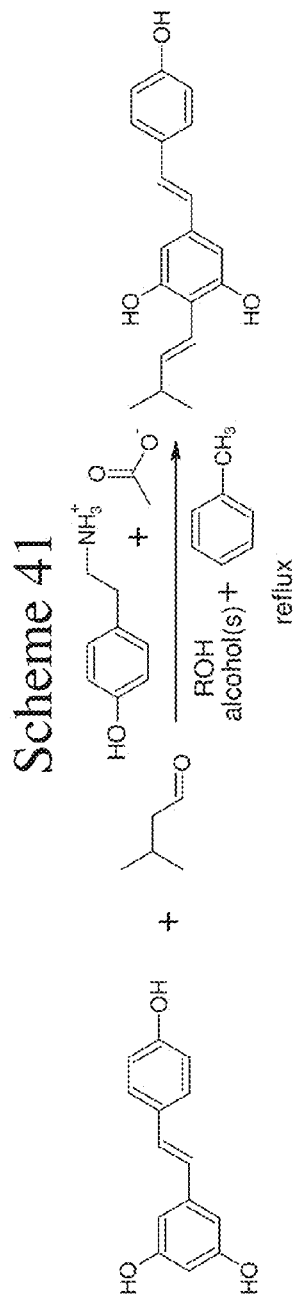
Figure 15:
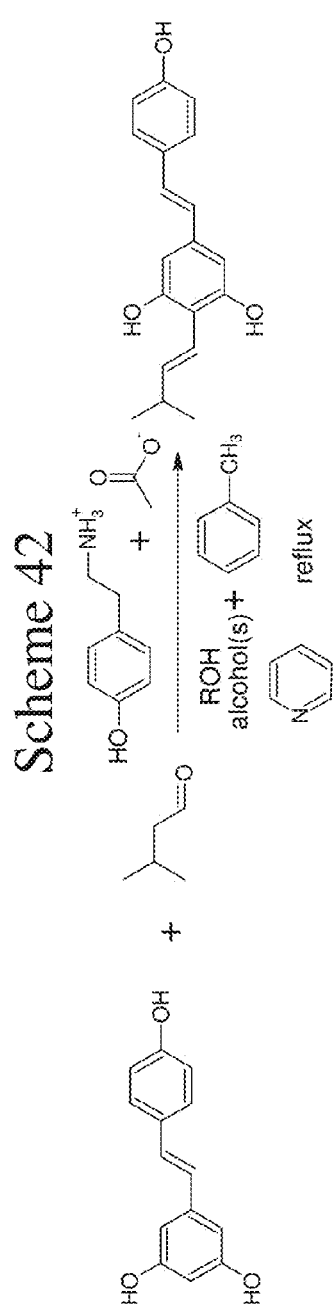
Figure 16:
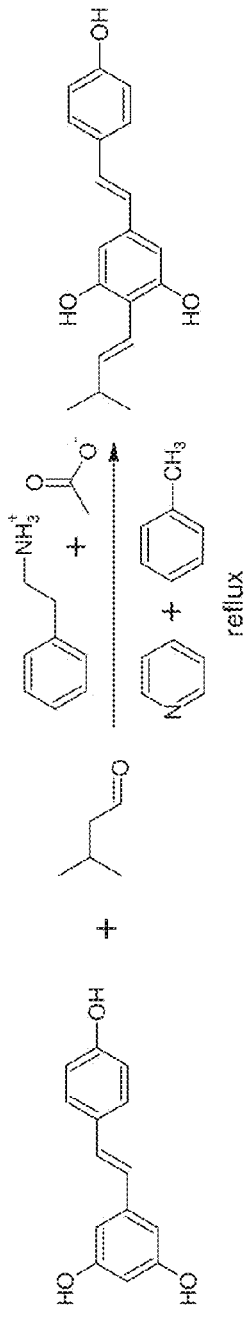
FIG. 16 is a diagram of embodiments of Schemes 43-45 comprising a chemical reaction of combining isovaleraldehyde and trans-resveratrol with a catalyst ($X_{15}$) and solvents ($Y_1$-$Y_3$).
Figure 16:
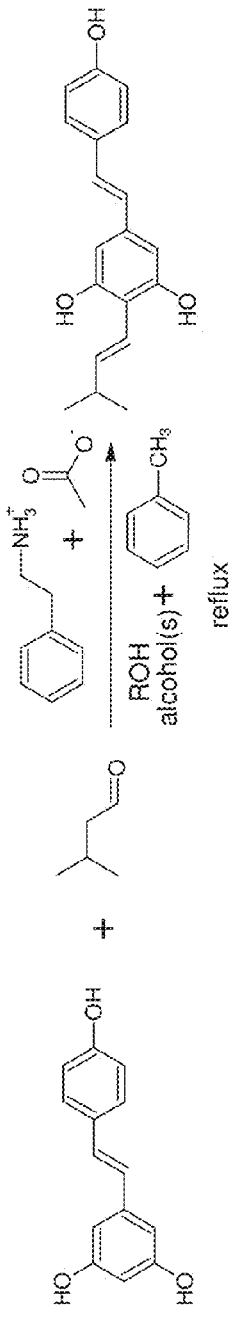
Figure 16:
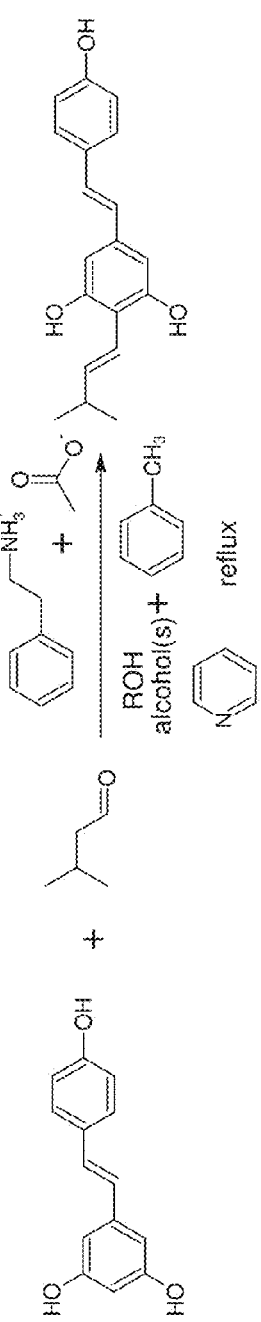
Figure 17:
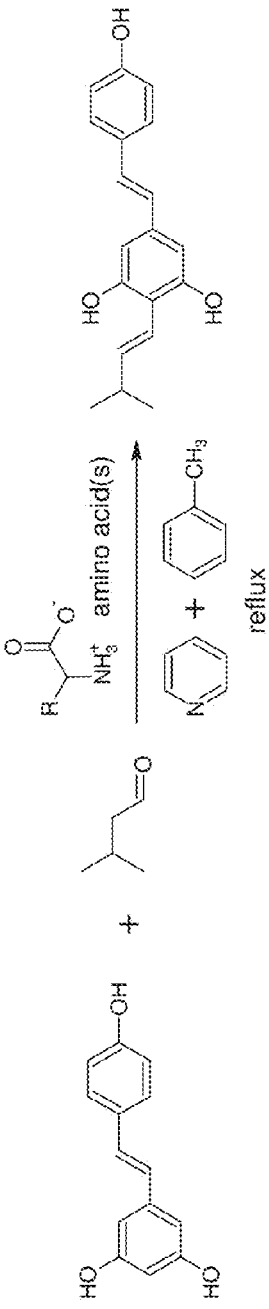
FIG. 17 is a diagram of embodiments of Schemes 46-48 comprising a chemical reaction of combining isovaleraldehyde and trans-resveratrol with a catalyst ($X_{16}$) and solvents ($Y_1$-$Y_3$).
Figure 17:
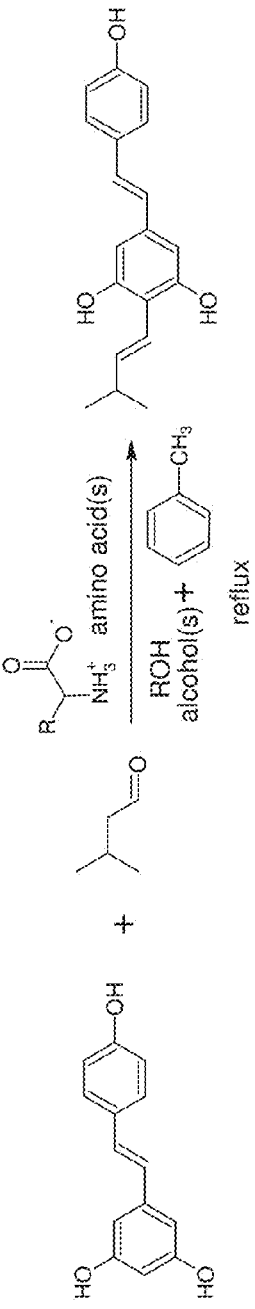
Figure 17:
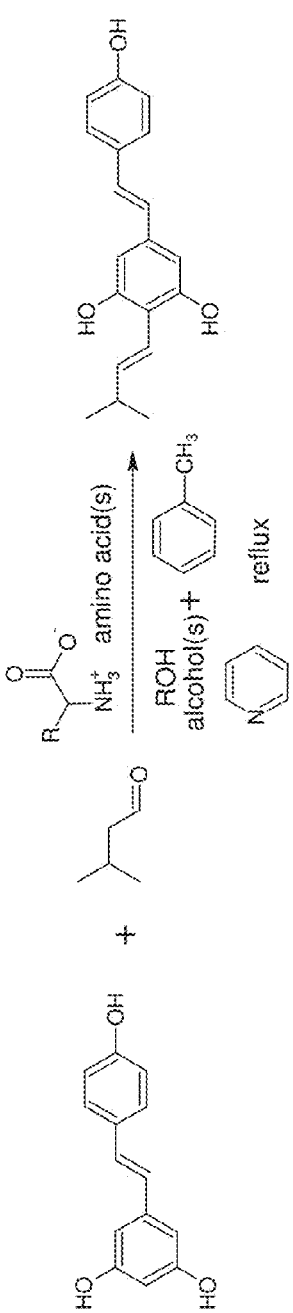
Figure 18:
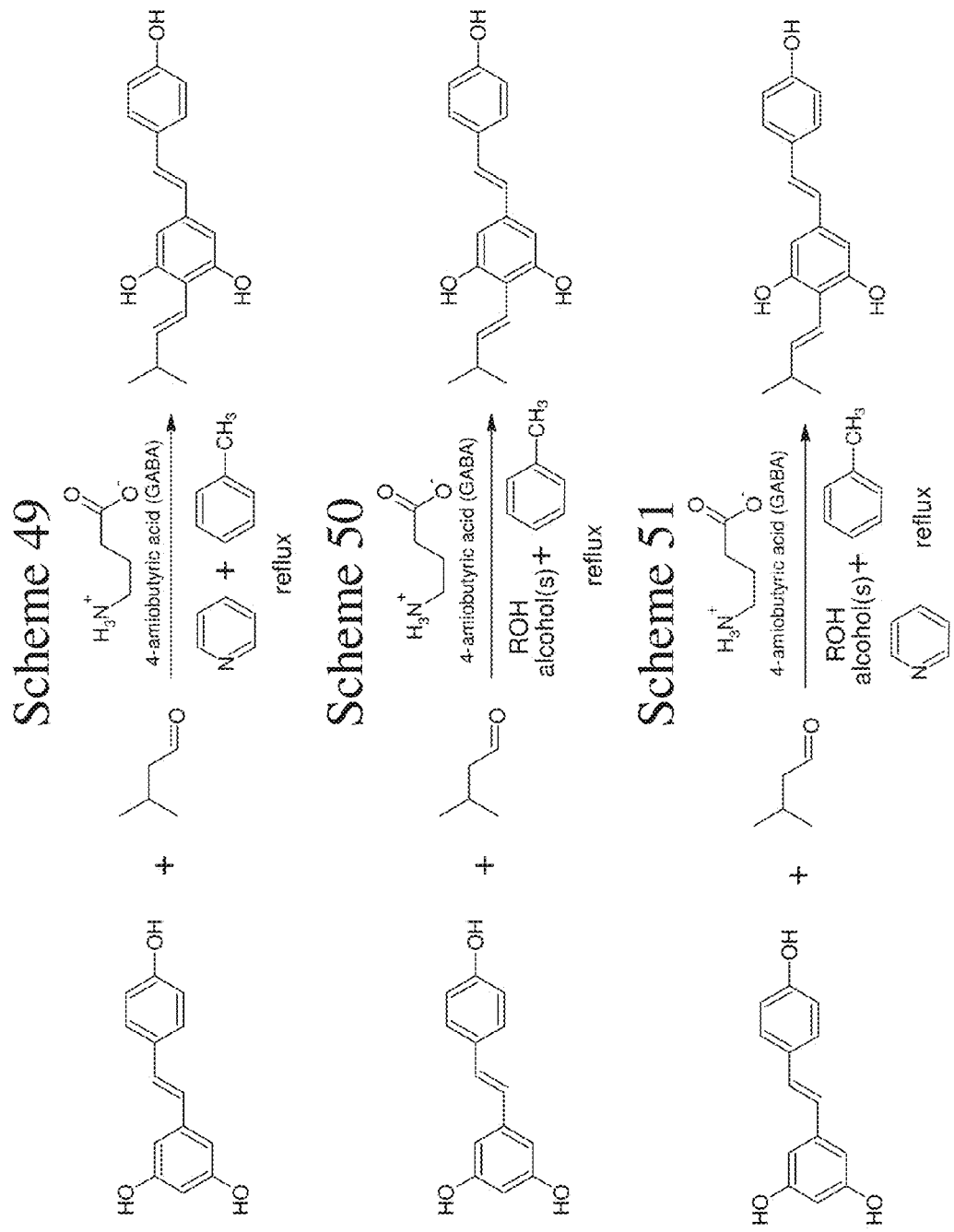
FIG. 18 is a diagram of embodiments of Schemes 49-51 comprising a chemical reaction of combining isovaleraldehyde and trans-resveratrol with a catalyst ($X_{17}$) and solvents ($Y_1$-$Y_3$).
Figure 19:
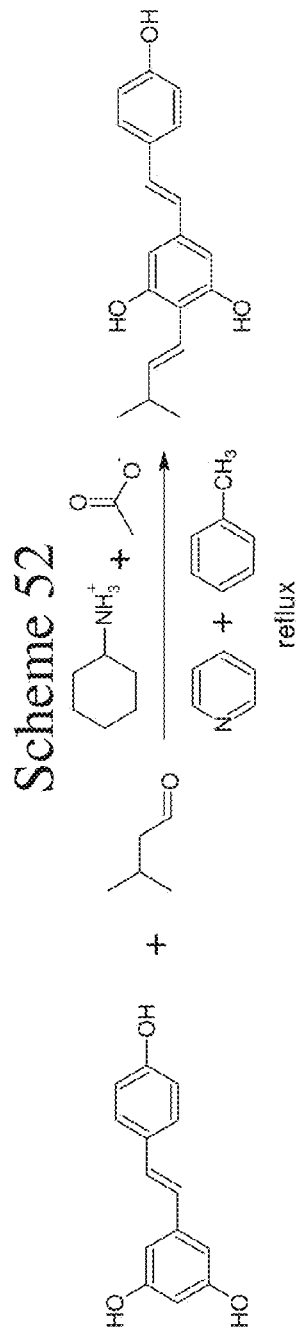
FIG. 19 is a diagram of embodiments of Schemes 52-54 comprising a chemical reaction of combining isovaleraldehyde and trans-resveratrol with a catalyst ($X_{18}$) and solvents ($Y_1$-$Y_3$).
Figure 19:
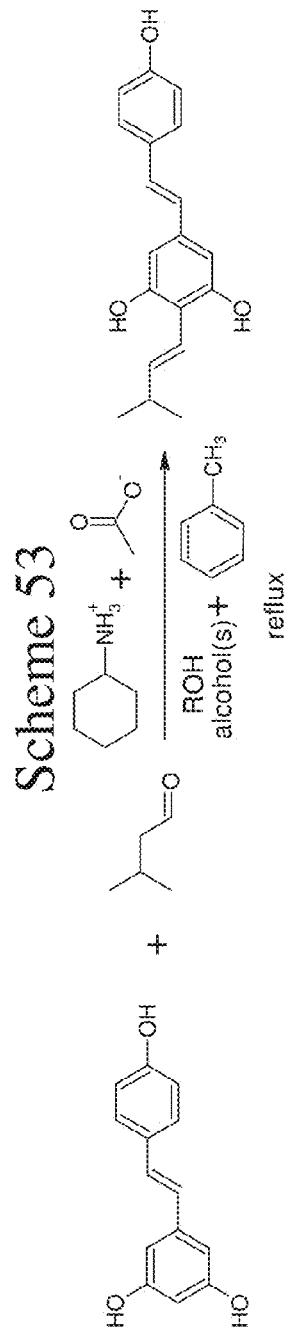
Figure 19:
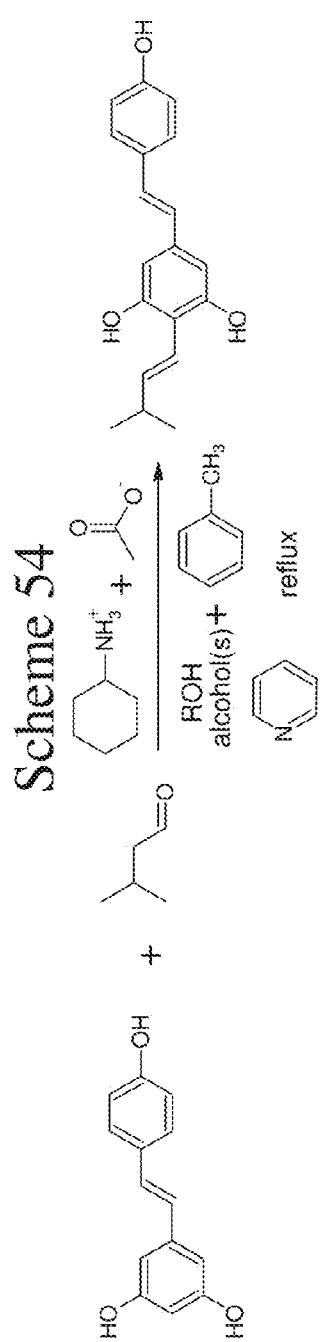
Figure 20:
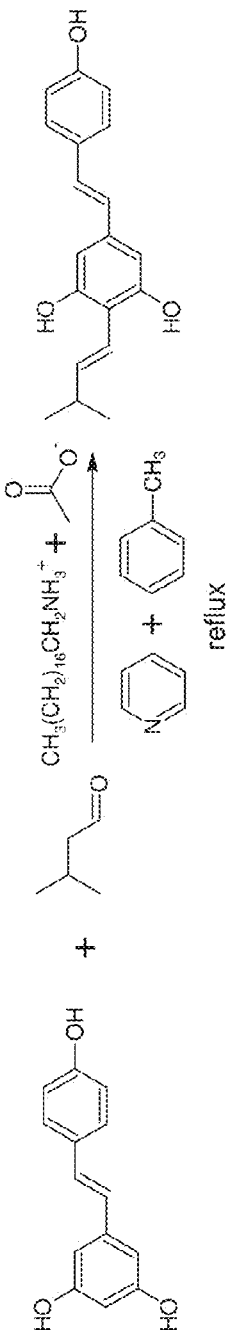
FIG. 20 is a diagram of embodiments of Schemes 55-57 comprising a chemical reaction of combining isovaleraldehyde and trans-resveratrol with a catalyst ($X_{19}$) and solvents ($Y_1$-$Y_3$).
Figure 20:
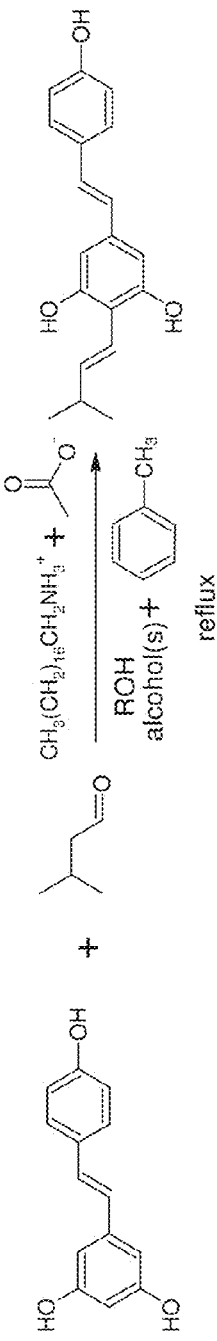
Figure 20:
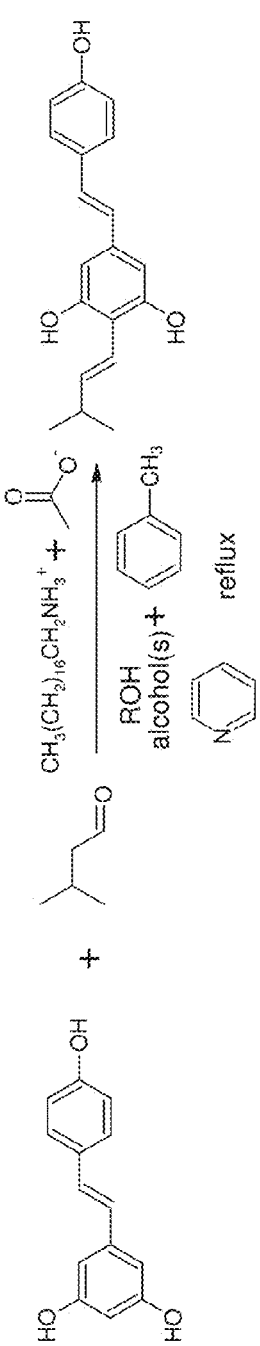
Figure 21:
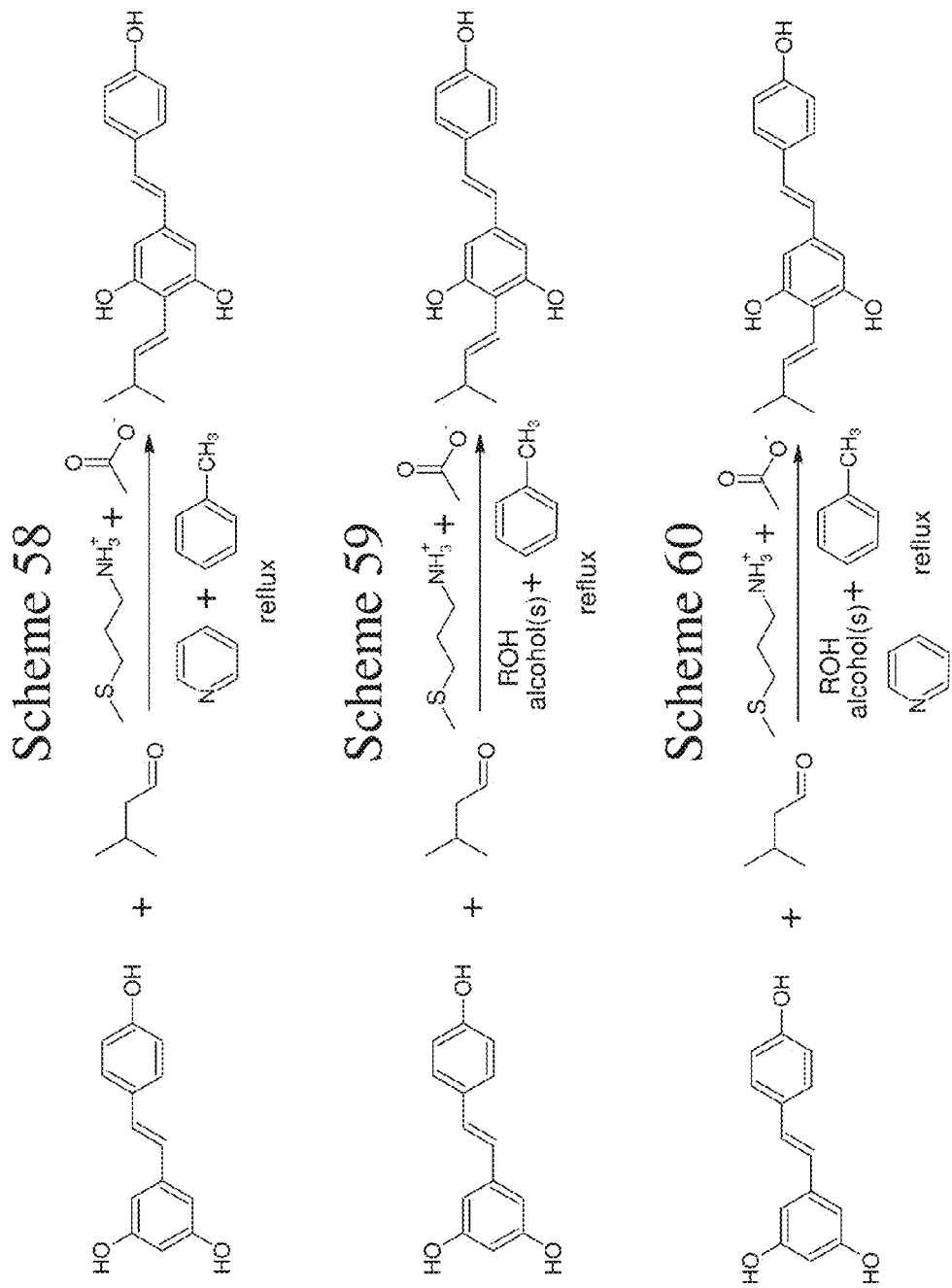
FIG. 21 is a diagram of embodiments of Schemes 58-60 comprising a chemical reaction of combining isovaleraldehyde and trans-resveratrol with a catalyst ($X_{20}$) and solvents ($Y_1$-$Y_3$).
Figure 22:
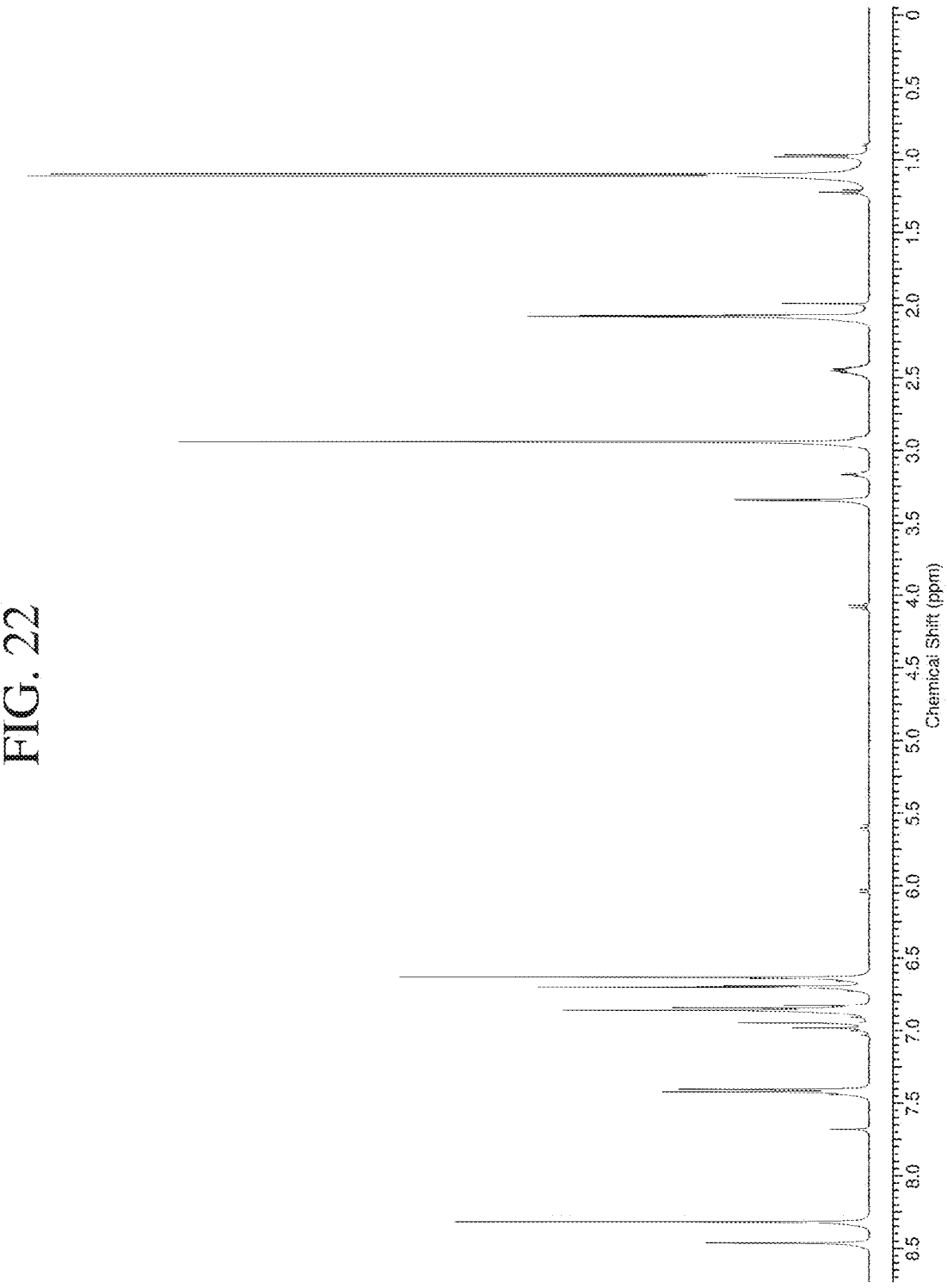
FIG. 22 is diagram of the synthetic, non-toxic trans-arachidin-3 $^1$H NMR Spectrum in the range of about 8.5 ppm to 0 ppm.
Figure 23:
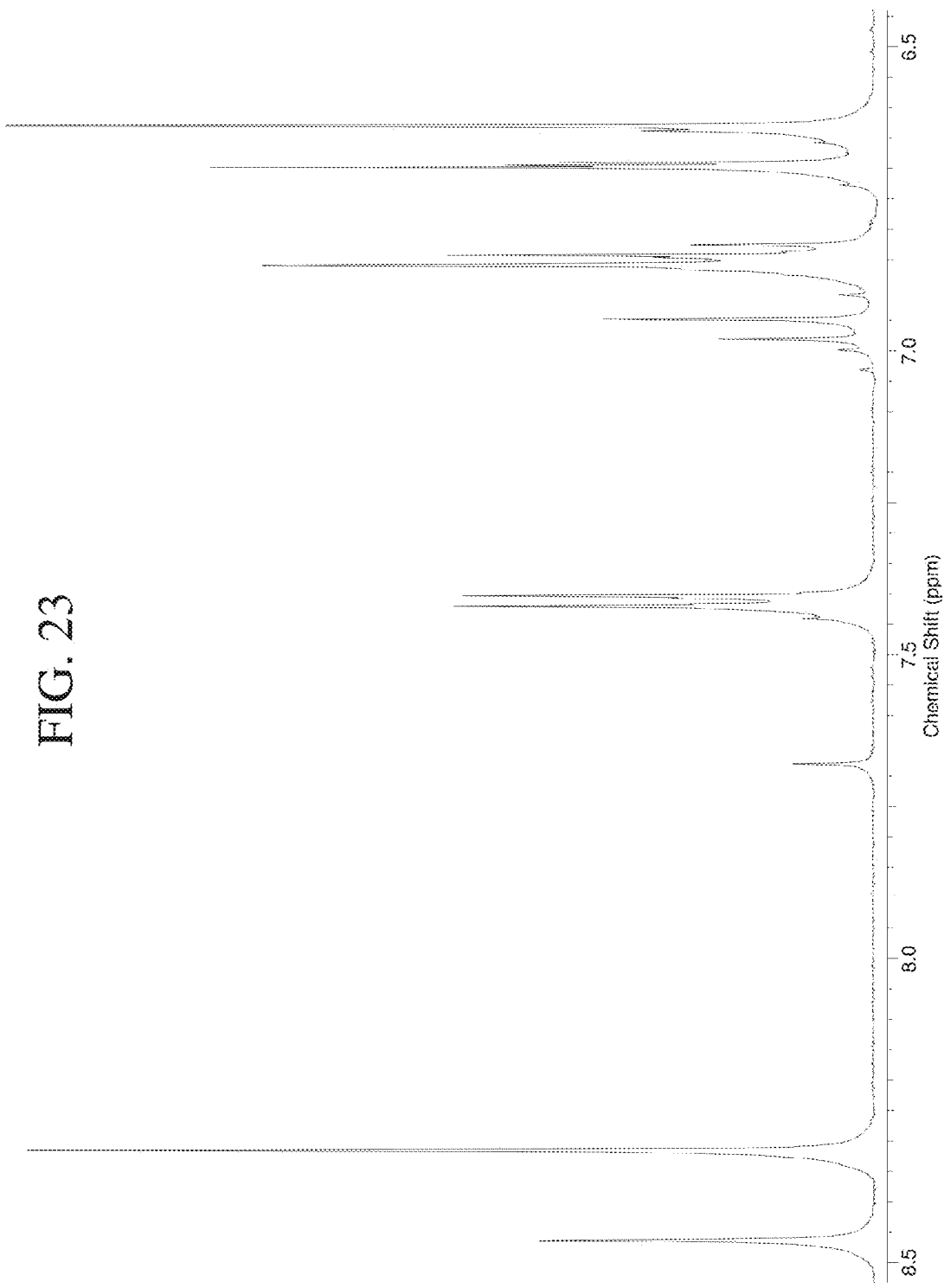
FIG. 23 is another diagram of trans-arachidin-3 $^1$H NMR Spectrum comprising a magnified view of FIG. 22 from about 8.5 ppm to 6.5 ppm.

The procedure for synthesizing Scheme 15 of FIG. 6 using a n-Propyl Amine Catalyst are as follows. Resveratrol (1.000 g, 0.00438 mol, MW 228.24 g·mol-1) was placed in a 250 mL round-bottom flask. To the flask was added: 136 mL of toluene, 54 mL of n-butanol, 10 mL of pyridine, and 10 mL of acetic acid, which was then swirled for several seconds to dissolve. 3-methylbutyraldehyde (1000 μL, ≥0.00438 mol, 86.13 g·mol-1) was pipetted into the flask, and then boiling chips (1 g) were added to prevent bumping. The catalyst, isopropyl amine (0.400 mL, density 0.1186 g·mL-1) was then pipetted shortly before attaching the still pot to a Dean-Stark apparatus. The solution was then refluxed for 24 hours while maintaining a temperature of 100-105 degrees Celsius. Approximately, 1-2 mL of water was observed in the trap following the reaction. The solution was allowed to cool to room temperature, and then concentrated using a rotary evaporator. Thin layer chromatography and high performance liquid chromatography was used to determine the reaction yield. The reaction yield of trans-arachidin-3 for this catalyst was 49.9% or 0.648 grams.

Scheme 15

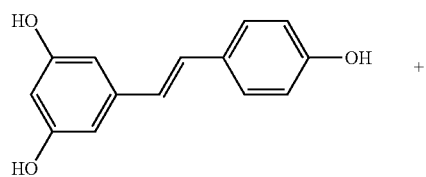

14

-continued

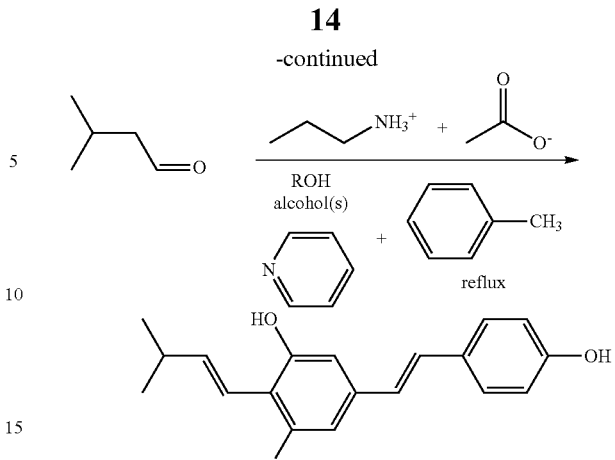

Methods of Use of the Synthesized, Non-Toxic, Trans-Arachidin-3

Diseases and Disorders

The synthetic trans-arachidin-3 produced by the one-reaction step, one still pot methods disclosed herein, is non-toxic and thus safe for use in treating and/or preventing diseases and disorders in mammalian subjects, such as humans and domesticated animals (e.g. canines, equines, cats, etc.). Treatment objectives include amelioration of symptoms, curing, preventing, halting, slowing, etc. of the disease or disorder for which the subject received the synthetic, non-toxic trans-arachidin-3 such that a therapeutic effect is experienced in the subject.

The types of diseases and disorders for which the synthetic trans-arachidin-3 produced by methods disclosed herein, include those for which other members of the stilbenoid family (e.g. resveratrol) are believed, or have been scientifically shown with in vitro and/or in vivo data, to have therapeutic efficiency.

Applicable diseases and disorders suitable for administering the synthetic trans-arachidin-3 produced by the methods disclosed herein comprise, by way of non-limiting examples: cancer, coronary heart disease, Alzheimer's, diabetes, hypertension, inflammation, antibacterial, and obesity. Because of the high degree of similarity between the chemical structure of trans-resveratrol and trans-arachidin-3 (see FIG. 1A versus FIG. 1B), they are believed to react in the same or a substantially similar manner when administered to a mammal, such as a human. Therefore, the types of diseases and disorders, routes of administration, doses, and so forth that are applicable to resveratrol, or other stilbenoids, are thus applicable to the synthetic trans-arachidin-3 disclosed herein. Likewise, co-administration of other known stilbenoids (e.g. resveratrol) with the synthetic trans-arachidin-3 to a mammal, such as a human, is believed to produce an unexpected synergistic therapeutic effect for the treatment of the stated diseases and disorders.

Resveratrol has been previously shown to be protective against oxidative stress, inflammation, and the development of cardiovascular diseases, diabetes, neurodegenerative diseases, and cancer. Resveratrol also in known to play a prominent role in the prevention of neurodegenerative diseases such as Alzheimer's disease, Parkinson's disease, cerebral ischemia, as well as Huntington's disease because resveratrol enters the blood stream after the formation of glucuronide conjugates and readily passes through the blood brain barrier. (see Rege et. al., "Neuroprotective effects of resveratrol in Alzheimer disease pathology", *Frontiers of Aging Neuroscience, September* 2014, Volume 6, Article 218: 1-12).

Additionally, there is ample scientific evidence for the ability of arachidin and resveratrol to provide a therapeutic benefit for the treatment of the diseases and disorders. For example, arachidin and resveratrol have demonstrated antioxidant and anti-inflammatory activity. Abbott J et. al., determined the antioxidant activity of these compounds using the thiobarbituric acid reactive substances (TBARS) assay, and by using the 3-(4,5-dimethylthiazol-2-yl)-2,5-diphenyltetrazolium bromide (MTT) assay. Oxidation was inhibited at a 14, 7, and 14 µM doses for CPC-purified resveratrol, arachidin-1, and arachidin-3, respectively. Arachidin-1 and arachidin-3 demonstrated cytotoxicity at 27 and 55 µM in RAW 264.7 and HeLa cell lines (see Abbott J et. al., "Purification of resveratrol, arachidin-1, and arachidin-3 from hairy root cultures of peanut (*Arachis hypogaea*) and determination of their antioxidant activity and cytotoxicity", *Biotechnol Prog.* 2010 September-October; 26(5): 1344-51.) (See also Brents L. K. et. al., "Natural prenylated resveratrol analogs arachidin-1 and -3 demonstrate improved glucuronidation profiles and have affinity for cannabinoid receptors", *Xenobiotica.* 2012 February; 42(2): 139-156).

Likewise, Chang J C et al. demonstrated that the compounds were effective in inhibiting PGE2- or NO-mediated inflammation and NF-kappaB- or C/EBPdelta-mediated inflammatory gene expression (see Chang J C et. al., "Biosynthesis enhancement and antioxidant and anti-inflammatory activities of peanut (*Arachis hypogaea* L.) arachidin-1, arachidin-3, and isopentadienylresveratrol", *J Agric Food Chem.* 2006 Dec. 27; 54(26):10281-7).

Therefore, the various embodiments of the present disclosure comprise a method of supplementing the diet of, or administering a pharmaceutical compound or composition to, a mammal suffering from one or more of these diseases and disorders. Methods disclosed herein further comprise administering to a mammal a dietary composition which may comprise a carrier, or not, and a therapeutic effective amount of the synthetic arachidin-3 produced by the methods disclosed herein, or a pharmaceutically acceptable salt thereof.

When utilizing the synthetic trans-arachidin-3 disclosed herein for the treatment of type I or type II diabetes, the formulation may further comprise other stibenoids and/or other antidiabetic, antihyperglycemic or blood glucose lowering agent including, such as: a biguanide such as metformin or buformin; a sulfonylurea such as acetohexamide, chlorpropamide, tolazamide, tolbutamide, glyburide, glypizide or glyclazide; a thiazolidinedione such as troglitazone; an alpha-glucosidase inhibitor such as acarbose or miglitol; a Pradrenoceptor agonist such as PL-316, 243, etc., cholestyramine, clofibrate, colestipol, fluvastatin, gemfibrozil, lovastatin, niacin, pravastatin, probucol, psyllium hydrophilic muccilloid, simvastatin, and sodium dichloro acetate.

Alternatively, the compositions comprising a synthetic trans-arachidin-3 produced via the methods disclosed herein, or a pharmaceutically acceptable salt thereof, can be administered in combination with, prior to, concurrent with or subsequent to the administration of another antidiabetic, antihyperglycemic, or anti-lipidemic agent.

When utilizing the synthetic trans-arachidin-3 produced via the methods disclosed herein for the progression of atherosclerotic cardiovascular diseases and hypertension in subjects, the synthetic arachidin-3 may be administered alone, or with other stilbenoids and/or other compounds that have shown therapeutic efficacy in lowering serum triglyceride or cholesterol. Such compounds are well known in the art, and comprise by way of non-limiting examples: (A) fibrates; (B) HMG-CoA reductase inhibitors; (C) inhibitors of cholesterol absorption; (D) squalene synthesis inhibitors; (E) LDL catabolism enhancers; and (F) angiotensin converting enzyme inhibitors.

Kits, Compositions, Compounds

The various embodiments disclosed herein further comprise kits for methods of making and using, and compositions and compounds for practicing the subject methods, as described above. The kit's components are configured to add U.S. Food and Drug Administration (F.D.A.) approved solvents, catalysts, and reagents for performing any steps in the methods described herein to chemically produce and therapeutically use synthetic, non-toxic trans-arachidin-3 that is derived from resveratrol via these one-reaction, one pot methods disclosed herein. The various components of the kits may be present in separate containers, or certain compatible components may be pre-combined into a single container, as desired.

The various trans-arachidin-3 compositions produced via the methods disclosed herein may further comprise at least one excipient, such as a buffering agent, a preservative, a stabilizer, a binder, a compaction agent, a lubricant, a dispersion enhancer, a disintegration agent, a flavoring agent, a sweetener, a coloring agent, and any combination thereof. The weight fraction of the excipient or combination of excipients in the compositions may be about 30% or less, about 25% or less, about 20% or less, about 15% or less, about 10% or less, about 5% or less, about 2%, or about 1% or less of the total weight of the therapeutic composition.

In addition to above-mentioned components, the subject kits typically further include instructions for using the components of the kit to practice the subject methods, such as for the disclosed methods of treatment and/or method of synthesizing. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Although the various embodiments of the present disclosure have been described in some detail by way of illustration and example for purposes of clarity of understanding, it is readily apparent to artisan in light of the teachings of this invention that certain changes and modifications may be made thereto without departing from the spirit or scope of the disclosure.

Routes of Administration and Formulations

The synthetic, non-toxic trans-arachidin-3 compositions and compounds produced by the one-reaction, one still pot methods disclosed herein may be formulated into a variety of forms and administered by a number of different routes of administration. The compositions and compounds may be administered orally, topically, mucosally or parenterally, in formulations containing conventionally acceptable carriers, adjuvants, and vehicles as desired. The term "parenteral" as used herein includes subcutaneous, intravenous, intramuscular, or intrasternal injection, or infusion techniques. In an exemplary embodiment, the compounds of the present disclosure are administered: 1) orally in a solid (e.g. pill, tablet, or food product) or in a solution (e.g. nutraceutical drink); and, 2) topically (e.g. ointment, lotion, cream, cosmetic, etc.).

The amount of the synthetic arachidin-3 in the various dosage forms disclosed herein (e.g. solid tablets, liquid and solid food products) is sufficient to produce a therapeutic benefit for the intended disease or disorder being treated or prevented or to enhance the user's overall health. For example, the weight fraction of the synthetic arachidin-3 may be about 80% or less, about 70% or less, about 60% or less, about 50% or less, about 40% or less, about 30% or less, about 20% or less, about 10% or less, about 5% or less, about 2%, or about 1% or less of the total weight of the composition. Additionally, for example, the amount of the synthetic, non-toxic transarachidin-3 in the consumed food and/or drink is at least about 0.1 grams per dietary unit, and can readily be determined by a skilled artisan without engaging in undue experimentation.

In an embodiment, humans may consume up to about two grams of synthetic, non-toxic trans-arachidin-3 (2,000 milligrams) or more a day to achieve the intended therapeutic effect. In another embodiment, the subject is administered 10-100 µM daily, weekly, etc. (see Rege et. al., "Neuroprotective effects of resveratrol in Alzheimer disease pathology", *Frontiers of Aging Neuroscience*, September 2014, Volume 6, Article 218: 1-12, wherein resveratrol (10-100 µM) was reported to exert neuroprotective effects in several studies citing (Richard et al., 2011)).

In most instances, the required dosage is determined by one or more of the following: the age, weight, and gender of the subject; the particular disease or disorder being treated or prevented; the severity of the disease or disorder; the duration of the treatment; the route of administration; and the specific compound or composition being employed.

Solid Dosage Forms

Solid dosage forms for oral administration of the synthetic arachidin-3 compositions and compounds produced by the one-step methods disclosed herein may include capsules, tablets, caplets, pills, troches, lozenges, powders, and granules. A capsule typically comprises a core material comprising a composition of synthetic, non-toxic transarachidin-3 and a shell wall that encapsulates the core material. The core material may be solid, liquid, or an emulsion. The shell wall material may comprise soft gelatin, hard gelatin, or a polymer. Suitable polymers include, but are not limited to: cellulosic polymers such as hydroxypropyl cellulose, hydroxyethyl cellulose, hydroxypropyl methyl cellulose (HPMC), methyl cellulose, ethyl cellulose, cellulose acetate, cellulose acetate phthalate, cellulose acetate trimellitate, hydroxypropylmethyl cellulose phthalate, hydroxypropylmethyl cellulose succinate and carboxymethylcellulose sodium; acrylic acid polymers and copolymers, preferably formed from acrylic acid, methacrylic acid, methyl acrylate, ammonio methylacrylate, ethyl acrylate, methyl methacrylate and/or ethyl methacrylate (e.g., those copolymers sold under the trade name "Eudragit"); vinyl polymers and copolymers such as polyvinyl pyrrolidone, polyvinyl acetate, polyvinylacetate phthalate, vinylacetate crotonic acid copolymer, and ethylene-vinyl acetate copolymers; and shellac (purified lac). Some such polymers may also function as taste-masking agents.

Tablets, pills, and the like comprising the synthetic arachidin-3 compositions and compounds produced by the one-reaction, one still pot methods disclosed herein may be compressed, multiply compressed, multiply layered, and/or coated. The coating may be single or multiple. In one embodiment, the coating material may comprise a polysaccharide or a mixture of saccharides and glycoproteins extracted from a plant, fungus, or microbe. Non-limiting examples include corn starch, wheat starch, potato starch, tapioca starch, cellulose, hemicellulose, dextrans, maltodextrin, cyclodextrins, inulins, pectin, mannans, gum arabic, locust bean gum, mesquite gum, guar gum, gum karaya, gum ghatti, tragacanth gum, funori, carrageenans, agar, alginates, chitosans, or gellan gum. In another embodiment, the coating material may comprise a protein. Suitable proteins include, but are not limited to, gelatin, casein, collagen, whey proteins, soy proteins, rice protein, and corn proteins. In an alternate embodiment, the coating material may comprise a fat or oil, and in particular, a high temperature melting fat or oil. The fat or oil may be hydrogenated or partially hydrogenated, and preferably is derived from a plant. The fat or oil may comprise glycerides, free fatty acids, fatty acid esters, or a mixture thereof. In still another embodiment, the coating material may comprise an edible wax. Edible waxes may be derived from animals, insects, or plants. Non-limiting examples include beeswax, lanolin, bayberry wax, carnauba wax, and rice bran wax. Tablets and pills may additionally be prepared with enteric coatings.

In one embodiment as a tablet or pill or capsule for oral administration, a vitamin comprising the non-toxic, synthetic trans-arachidin-3 disclosed herein may comprise other vitamins commonly found in a vitamin pill or capsule, such as: Vitamin A, C, D, E, K, $B_1$, $B_6$, $B_{12}$; Calcium; Thiamin; Riboflavin; Niacin; Folic Acid; Vitamin B-12; Biotin; Pantothenic Acid; Iodine; Magnesium; Zinc; Selenium; Copper; Manganese; Chromium; Potassium; Boron; Choline, and any combinations thereof.

In another embodiment as a tablet or pill or capsule for oral administration, the synthetic trans-arachidin-3 produced by the methods disclosed herein may be administered with only an excipient or other carrier (e.g. a dietary supplement comprising a daily administered pill of trans-arachidin-3 alone).

In another embodiment as a tablet or pill or capsule for oral administration, the synthetic, non-toxic trans-arachidin-3 produced by the methods disclosed herein may be combined with other stilbenoids (e.g. resveratrol).

In another embodiment as a tablet or pill or capsule for oral administration, the synthetic non-toxic trans-arachidin-3 produced by the methods disclosed herein may be combined with other agents that have been demonstrated to have a therapeutic effect for the same diseases and disorders that the arachidin-3 is being administered for. These other agents may be known in the art, and when combined with the synthetic, non-toxic trans-arachidin-3 they provide an unexpected synergistic therapeutic effect when administered to mammals suffering from that disease or disorder.

Food Product with the Synthetic Arachidin-3

Powders or granules or solids or semi-solids or liquids embodying the synthetic, non-toxic trans-arachidin-3 compositions and compounds produced by the methods disclosed herein may be incorporated into a food product.

In one embodiment, the food product may be a drink for oral administration, such as a nutraceutical, a fruit juice, a fruit drink, an artificially flavored drink, an artificially sweetened drink, a carbonated beverage, a sports drink, a liquid diary product, a shake, etc.

Other suitable means for oral administration include aqueous and non-aqueous solutions, emulsions, suspensions and solutions and/or suspensions reconstituted from non-effervescent granules, containing suitable solvents, preservatives, emulsifying agents, suspending agents, diluents, sweeteners, coloring agents, and flavoring agents.

The food product may also be a solid, semi-solid or soft foodstuff. Suitable non-limiting examples of a food product comprising the synthetic, non-toxic trans-arachidin-3 include: a sports or nutritional or protein or snack bar; a bakery item—e.g. a cookie, a brownie, a muffin, a cake, a pastry; a diary product—a yogurt, an ice cream or a frozen yogurt bar, a smoothie and the like.

It is noted that food products for use in the various embodiments are made in a manner (e.g. temperatures, mixing with other ingredients, etc.) that does not reduce, inactivate, or otherwise adversely affect the physiological activity of the synthetic, non-toxic trans-arachidin-3 when it is administered to a mammal for therapeutic benefits.

Cosmetic or Topical Treatment (Antibacterial, Anti-Inflammatory)

The various embodiments of the present disclosure further comprise methods for the treatment and prevention of skin conditions, such as inflammation and infections and skin cancer, comprising topically administering a pharmaceutical composition to a subject in need thereof, the pharmaceutical composition consisting essentially of, or comprising, an effective amount of the synthetic, non-toxic trans-arachidin-3 alone, or in combination with other therapeutic compounds, such as other stilbenoids (e.g. arachidin-1, resveratrol, etc.).

The embodiments further comprise a method for treatment of a subject suffering from a wound, infection, or inflammation the method comprising: providing a topical formulation comprising a carrier and a combination of active ingredients that includes at least one stilbenoid and at least one blood vessel dilator wherein the at least stilbenoid of the formulation is the synthetic, non-toxic trans-arachidin-3, in a stable emulsion; and applying the topical formulation to the skin of a subject suffering from a wound, infection, or inflammation so as to at least cause healing or accelerated healing of the wound, infection or inflammation.

Topically administering as used herein means applying a composition of the synthetic, non-toxic trans-arachidin-3 by directly laying on or spreading the composition on a subject's outer skin, scalp, or hair, e.g., by use of the hands or an applicator such as a wipe, mask (i.e., facial mask), roller, or spray. The composition is also "cosmetically acceptable"—meaning that all of the ingredients within the composition are suitable for use in contact with tissues (e.g., the skin or hair) without undue toxicity, incompatibility, instability, irritation, allergic response, or the like.

Particularly suitable formulations are formulations comprising an effective amount of the synthetic, non-toxic trans-arachidin-3 alone, or in combination with other therapeutic compounds, such as other stilbenoids (e.g. arachidin-1, resveratrol, etc.) for local delivery, such as topical formulations in the form of ointments, gels, creams, pastes, solutions, suspensions, lotions and emulsions.

Additional agents may be added to the formulation to increase therapeutic effectiveness in general or to enhance suitability for specific uses. These additional agents may include one or more of an antioxidant, such as: ascorbate (e.g. as a sodium or calcium salt); tocopherol; co-enzyme Q10; or combinations thereof.

The formulations may also have carrier substances, which may be inactive or may enhance the activity of the synthetic, non-toxic trans-arachidin-3 compounds. Examples of substances that may be used as carriers include acrylic acid, caprice glyceride, soybean or other vegetable oils, vitamin E, TPGS, silicone, glyceryl stearate, glycerin, oleic acid, acetyl alcohol, olive oil, ethyl operate, isopropyl microstate, propyl paraben, allantois, triethanolamine, acrylates (e.g., c10-30 alkyl acrylate copolymer), phenoxyethanol, hydroxypropyl methyl cellulose, and xantham gum. The formulation may include a stable emulsion of the active ingredients together with carriers.

The required dosage of the pharmaceutically acceptable agent will vary with the particular condition being treated, the severity of the condition, the duration of the treatment, the administration route and the specific compound being employed. By way on non-limiting examples, in a topical formulation the amount of the pharmaceutically acceptable arachidin-3 can typically range about 0.01% to about 10%, preferably from about 0.1% to about 5%, more preferably from about 0.2% to about 2%, even more preferably from about 0.5% to about 1.5%, by weight of the composition.

It will be appreciated that the methods and compositions and compounds of the present disclosure can be incorporated in the form of a variety of embodiments, only a few of which are disclosed herein. It will also be apparent for the expert skilled in the field that other embodiments exist and do not depart from the spirit of the invention. Thus, the described embodiments are illustrative and should not be construed as restrictive.

Accordingly, the preceding exemplifications merely illustrate the principles of the various embodiments. It will be appreciated that those skilled in the art will be able to devise various arrangements which, although not explicitly described or shown herein, embody the principles of the embodiments and are included within its spirit and scope. Furthermore, all examples and conditional language recited herein are principally intended to aid the reader in understanding the principles of the invention and the concepts contributed by the inventor to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the various embodiments, therefore, is not intended to be limited to the exemplary embodiments shown and described herein.

The technology illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the technology claimed. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 5%), and use of the term "about" at the beginning of a string of values modifies each of the values (i.e., "about 1, 2 and 3" refers to about 1, about 2 and about 3). Further, when a listing of values is described herein (e.g., about 50%, 60%, 70%, 80%, 85% or 86%) the listing includes all intermediate and fractional values thereof (e.g., 54%, 85.4%). Thus, it should be understood that although the present technology has been specifically disclosed by representative embodiments and optional features, modification and variation of the concepts herein disclosed may be resorted to by those skilled in the art, and such modifications and variations are considered within the scope of this technology.

REFERENCES

Abbott J et. al., "Purification of resveratrol, arachidin-1, and arachidin-3 from hairy root cultures of peanut (*Arachis hypogaea*) and determination of their antioxidant activity and cytotoxicity", Biotechnol Prog. 2010 September-October; 26(5):1344-51.

Annand, Aretha. "Cancer is a Preventable Disease that Requires Major Lifestyles Change," *Pharmaceutical Research*, 2008, 25:2097-2116.

Chang J C et. al., "Biosynthesis enhancement and antioxidant and anti-inflammatory activities of peanut (*Arachis hypogaea* L.) arachidin-1, arachidin-3, and isopentadienylresveratrol",

*J Agric Food Chem*. 2006 Dec. 27; 54(26):10281-7. Condor, J. et. al. "Induced biosynthesis of resveratrol and the prenylated stilbenoids arachidin-1 and arachidin-3 in hairy root cultures of peanut: Effects of culture medium and growth stage," *Plant Physiology and Biochemistry*, 2010, 48:310-318.

Baum, J. A, et. al. "Therapeutic potential of resveratrol: the in vivo evidence," *Nature Reviews Drug Discovery*, 2006, 5:493-506.

Brents, L. K., et. al. "Natural prenylated resveratrol analogs arachidin-1 and -3 demonstrate improved glucuronidation profiles and have affinity for cannabinoid receptors," *Xenobiotica*, 2012, 42(2):139-156.

Das S., Das D. K. (2007). Anti-inflammatory responses of resveratrol. *Inflamm. Allergy Drug Targets* δ 168-173.

Park, B. H., et. al. "Total Synthesis of Chiricanine A, Arahypin-1, trans-Arachidin-2, trans-Arachidin-3, and Arahypin-5 from Peanut Seeds," *Journal of Natural Products*, 2011, 74:644-649.

Rege et. al., "*Neuroprotective effects of resveratrol in Alzheimer disease pathology*", Frontiers of Aging Neuroscience, September 2014, Volume 6, Article 218: 1-12.

Stavric, Bozidar. "Role of Chemopreventers in Human Diet." *Clinical Biochemistry* 27.5 (1994): 319-32. Print.

What is claimed is:

1. A method of chemically synthesizing a non-toxic trans-arachidin-3, comprising:
    a. dissolving a first reagent of resveratrol into a solvent comprising an azeotropic mixture of toluene to create a composition;
    b. adding a second reagent isovaleraldehyde to the composition;
    c. adding a catalyst to the composition of step (b), wherein the catalyst is selected from the group consisting of a mixture of a primary alkylamine with acetic acid, a mixture of a primary hydroxyalkyl amine with acetic acid, and carboxy amine;
    d. refluxing the composition;
    e. purifying out a trans-arachidin-3 compound from the composition;
    f. wherein steps (a)-(d) are carried out in the same still pot; and
    g. wherein the purified composition of step (e) is safe for use in humans.

2. The method of claim 1, wherein the resveratrol is synthetic or naturally occurring resveratrol.

3. The method of claim 1, wherein the resveratrol is trans-resveratrol.

4. The method of claim 1, wherein the catalyst is selected from the group consisting of 1-amino-2-propanol, n-propyl amine, and ethanol amine.

5. The method of claim 1, wherein the solvent is an azeotropic mixture of toluene with one or more of the following compounds: pyridine, n-butanol, n-propanol, 2-propanol, 2-methyl-1-propanol, and any combination thereof.

6. The method of claim 1, wherein the catalyst, solvent, and reagents are approved by the Food and Drug Administration for use in humans.

7. The method of claim 1, wherein the purification comprises one or more of the following: column chromatography (neutral); high performance liquid chromatography (HPLC); high performance counter-current chromatography; recrystallization in hexanes and ethyl acetate, n-butanol, n-propanol, 2-propanol, or 2-methyl-1-propanol; and, solid-phase extraction using neutral alumina.

8. The method of claim 1, wherein the refluxing occurs for about 24 hours at about 100 to 105 degrees Celsius.

9. The method of claim 5, wherein the catalyst is 1-amino-2-propanol with acetic acid, and the solvent is a mixture of 27 volume percent n-butanol with 73 volume percent toluene.

* * * * *